(12) United States Patent
Liu

(10) Patent No.: US 11,684,672 B2
(45) Date of Patent: Jun. 27, 2023

(54) COMBINATIONS OF COPANLISIB WITH ANTI-PD-1 ANTIBODY

(71) Applicant: BAYER PHARMA AKTIENGESELLSCHAFT, Berlin (DE)

(72) Inventor: Ningshu Liu, Berlin (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 520 days.

(21) Appl. No.: 16/488,112

(22) PCT Filed: Feb. 22, 2018

(86) PCT No.: PCT/EP2018/054376
§ 371 (c)(1),
(2) Date: Aug. 22, 2019

(87) PCT Pub. No.: WO2018/153980
PCT Pub. Date: Aug. 30, 2018

(65) Prior Publication Data
US 2020/0114001 A1    Apr. 16, 2020

(30) Foreign Application Priority Data

Feb. 24, 2017    (EP) .................................... 17157835

(51) Int. Cl.
| | | |
|---|---|---|
| *A61K 31/5377* | (2006.01) | |
| *A61K 39/395* | (2006.01) | |
| *A61P 35/00* | (2006.01) | |
| *A61K 31/519* | (2006.01) | |
| *A61K 39/00* | (2006.01) | |
| *C07D 243/34* | (2006.01) | |
| *A61K 47/68* | (2017.01) | |

(52) U.S. Cl.
CPC ...... *A61K 39/39558* (2013.01); *A61K 31/519* (2013.01); *A61K 31/5377* (2013.01); *A61P 35/00* (2018.01); *A61K 47/6801* (2017.08); *A61K 2039/545* (2013.01); *C07D 243/34* (2013.01)

(58) Field of Classification Search
CPC ............................. A61K 39/39; A61K 31/5377
See application file for complete search history.

(56) References Cited

U.S. PATENT DOCUMENTS

2016/0296633 A1    10/2016  Goldenberg et al.

FOREIGN PATENT DOCUMENTS

| WO | 2004/029055 A1 | 4/2004 |
| WO | 2008/070150 A1 | 6/2008 |
| WO | 2017/153220 A1 | 9/2017 |

OTHER PUBLICATIONS

Vippagunta et al. (2001) Wolff (1995).*
McMahon et al (2000) Banker et al. (1997).*
Pinedo et al. (2000).*
Request for Project Team Member Application for CUndcting Clinical Trials Using Copanlisib (NSC#784727) (2016).*
International Search Report, PCT Appl. No. PCT/EP2018/054376; dated May 24, 2018.
Project Team Member Application—Copanlisib, Request for Project Teammember Application for Conducting Clinical Trials Using Copanlisib (NSC #784727), NRG Oncology: Copanlisib PTMA Announcement, XP002780848, Dec. 2016. Retrieved from the Internet: https:nrgoncology.org/Portals/0/News/Announcements/Sopanlisib_NSC784727_12212016_%20PTMA.pdf (Retrieved May 7, 2018).
Philips, G.K. et al., Therapeutics Uses of Anti-PD-1 and Anti-PD-LI Antibodies, International Immunology, vol. 27, No. 1, Oct. 16, 2014, pp. 39-46, The Japanese Society for Immunology.
Liu, N. et al., Copanlisib in Combinaion with Anti-PD-1—Induces Regression in Animal Tumor Models Insensitive or Resistant to the Monotherapies of PI3K and Checkpoint Inhibitors, May 27, 2017. Retrieved from the Internet: https://onlinelibrary.wiley.com/doi/fu11/10.1002/hon.2438_123 (Retrieved on May 7, 2018).

* cited by examiner

*Primary Examiner* — Paul V Ward
(74) *Attorney, Agent, or Firm* — Quarles & Brady LLP

(57) ABSTRACT

The present invention relates to: * combinations of: component A: one or more 2,3-dihydroimidazo[1,2-c]quinazoline compounds of general formula (A1) or (A2) as defined herein, or a physiologically acceptable salt, solvate, hydrate or stereoisomer thereof; component B: anti-Programmed Cell Death Protein 1 (also referred to as "PD-1" or "CD279" (cluster of differentiation 279)) antibody (anti-PD-1 mAb) as defined herein; in which optionally some or all of the components are in the form of a pharmaceutical formulation which is ready for use to be administered simultaneously, concurrently, separately or sequentially; independently of one another by the oral, intravenous, topical, local installations, intraperitoneal or nasal route; * use of such combinations for the preparation of a medicament for the treatment or prophylaxis of a cancer; and * a kit comprising such a combination.

34 Claims, 6 Drawing Sheets

Responses in the A20 tumor model treated with Cpd A and/or Cpd B

|  | PR+CR | SD | PD |
|---|---|---|---|
| Vehicle | 0 | 0 | 100% |
| Ctrl Ab | 0 | 0 | 100% |
| Cpd A | 0 | 0 | 100% |
| Cpd B | 0 | 0 | 100% |
| Cpd A + Cpd B | 0 | 37.5% | 62.5% |
| CpdA -> Cpd B | 75.0% | 12.5% | 12.5% |
| Cpd B-> Cpd A | 12.5% | 12.5% | 75.0% |

PR: partial response; CR: complete response;
SD: stable disease; PD: progressive disease Anti-tumor efficacy in CT26 CRC model

| Group | TGI | RR |
|---|---|---|
| Ctrl Ab | 18% | 0% |
| Cpd A | 71% | 0% |
| Cpd B | 64% | 14% |
| Cpd A → Cpd B | 98% | 100% |

Fig. 2B

COMBINATIONS OF COPANLISIB WITH ANTI-PD-1 ANTIBODY

CROSS REFERENCE TO RELATED APPLICATIONS

This application is the U.S. national stage entry under 35 U.S.C. 371 of PCT/EP2018/054376 filed Feb. 22, 2018, which is hereby incorporated by reference herein, which claims benefit of priority to European Patent App. No. 17157835.4 filed on Feb. 24, 2017.

The present invention relates to combinations of:
component A: one or more 2,3-dihydroimidazo[1,2-c]quinazoline compounds of general formula (A1) or (A2) as defined herein, or a physiologically acceptable salt, solvate, hydrate or stereoisomer thereof;
and
component B: anti-Programmed Cell Death Protein 1 (also referred to as "PD-1" or "CD279" (cluster of differentiation 279)) antibody (anti-PD-1 mAb); and, optionally,
component C: one or more further pharmaceutical agents;
in which optionally either or both of components A and B in any of the above-mentioned combinations are in the form of a pharmaceutical formulation which is ready for use to be administered simultaneously, concurrently, separately or sequentially. The components may be administered independently of one another by the oral, intravenous, topical, local installations, intraperitoneal or nasal route.

Another aspect of the present invention relates to the use of such combinations as described supra for the preparation of a medicament for the treatment or prophylaxis of a cancer, particularly cancers with altered activation of PI3K pathway and/or particular PI3K isoform(s) induced modulation of immune response, which not only provide survival signaling to tumor cells but also cause impaired anti-tumor immunity and/or the resistance to the cancer immune therapies. The applicable cancer indications are, but not limited to, colorectal cancer, lung cancer, breast cancer, prostate cancer, bladder cancer, gastric cancer, head and neck cancer, liver cancer, brain cancer, melanoma, ovarian cancer, pancreatic cancer, kidney cancer, endometrial cancer, lymphoma, leukemia, etc.

In a further aspect, the present invention relates to a kit comprising a combination of
component A: one or more 2,3-dihydroimidazo[1,2-c]quinazoline compounds of general formula (A1) or (A2) as defined herein, or a physiologically acceptable salt, solvate, hydrate or stereoisomer thereof;
and
component B: anti-Programmed Cell Death Protein 1 (also referred to as "PD-1" or "CD279" (cluster of differentiation 279)) antibody (anti-PD-1 mAb);
in which optionally either or both of said components A) and B) in any of the above-mentioned combinations are in the form of a pharmaceutical formulation which is ready for use to be administered simultaneously, concurrently, separately or sequentially. The components may be administered independently of one another by the oral, intravenous, topical, local installations, intraperitoneal or nasal route.

BACKGROUND OF THE INVENTION

Combination of PI3K Inhibitors and Anti-Programmed Cell Death Protein 1 (Also Referred to as "PD-1" or "CD279" (Cluster of Differentiation 279)) Antibodies (anti-PD-1 mAb)

Cancer is the second most prevalent cause of death in the United States, causing 450,000 deaths per year. While substantial progress has been made in identifying some of the likely environmental and hereditary causes of cancer, there is a need for additional therapeutic modalities that target cancer and related diseases. In particular there is a need for therapeutic methods for treating diseases associated with dysregulated growth/proliferation.

Cancer is a complex disease arising after a selection process for cells with acquired functional capabilities like enhanced survival/resistance towards apoptosis and a limitless proliferative potential. Thus, it is preferred to develop drugs for cancer therapy addressing distinct features of established tumors.

The PI3K signaling pathway is one of the prominent pathways that promote tumor cell survival. PI3K is activated by many cancer related receptor tyrosine kinases (e.g. VEGFR, PDGFR, EGFR, HER2/3, or IGF-1R), cell adhesion molecules, GPCR, and oncogenic proteins (such as Ras). The PI3K pathway activation by genetic alteration of PI3K (activation mutation and/or amplification) and/or loss-of-function of the tumour suppressor PTEN are frequently found in many tumors. Furthermore, activation of PI3K is one of the major mechanisms causing the resistance of tumors to radio-, chemo- and targeted therapeutics.

Once PI3K is activated, it catalyzes the generation of PIP3 from PIP2. The biological active PIP3 binds to the pleckstrin homology (PH) domains of PDK-1, AKT, and other PH-domain containing proteins, such as Rho and PLC. As the consequence of binding to PIP3, these proteins are translocated to the cell membrane and are subsequently activated to induce tumor cell proliferation, survival, invation and migration.

In addition to the roles in tumor cells, PI3K also regulate the activity of the tumor stroma cells (cells that form part of the tumor mass but are not malignantly transformed). The stroma cells include (a) the vasculature, (b) infiltrating immune cells, (c) fibroblasts and (d) other connective tissue. Recent data indicate that the four class I PI3K isoforms have both redundant and distinct roles in regulating the PI3K signalling in each of these stromal elements. The complexity and/or difficulty in predicting the final outcomes of PI3K inhibitors have been realized, particularly with regard to different isoform profiles and/or other technical properties of PI3K inhibitors.

Programmed cell death protein 1, also known as PD-1 and CD279 (cluster of differentiation 279), is a protein that in humans is encoded by the PDCD1 gene [see: Shinohara T, Taniwaki M, Ishida Y, Kawaichi M, Honjo T (October 1994). "Structure and chromosomal localization of the human PD-1 gene (PDCD1)". Genomics 23 (3): 704-6. doi:10.1006/geno.1994.1562. PMID 7851902]; [see also: "Entrez Gene: PDCD1 programmed cell death 1"].

PD-1 is a cell surface receptor that belongs to the immunoglobulin superfamily and is expressed on T cells pro-B cells, macrophages [see: "Entrez Gene: PDCD1 programmed cell death 1"]. PD-1 binds two ligands, PD-L1 and PD-L2. PD-1, functioning as an immune checkpoint, plays an important role in down regulating the immune system by preventing the activation of T-cells, which in turn reduces immunity and promotes tolerance. The inhibitory effect of PD-1 is accomplished through a dual mechanism of promoting apoptosis (programmed cell death) in antigen specific T-cells in lymph nodes while simultaneously reducing apoptosis in regulatory T cells (suppressor T cells) [see: Francisco L M, Sage P T, Sharpe A H (July 2010). "The PD-1 pathway in tolerance and immunity". Immunological Reviews 236: 219-42. doi:10.1111/j.1600-065X.2010.00923.x. PMC 2919275. PMID 20636820]; [see also: Fife B T, Pauken K E (January 2011). "The role of the PD-1 pathway in autoimmunity and peripheral tolerance". Annals of the New York Academy of Sciences 1217: 45-59. doi:10.1111/j.1749-6632.2010.05919.x. PMID 21276005]. Base on these rationale, recently, a new class of drugs that block PD-1, the PD-1 inhibitors, activate the immune system to attack tumors and are successfully developed for the treatment of some types of cancer [see: Weber J (October 2010). "Safety, activity, and immune correlates of anti-PD-1 antibody in cancer". The New England Journal of Medicine 366 (26): 2443-54]. Treatment of patients with melanoma, lung cancer or bladder cancer induced objective responses (1-3). However, the majority of patients still fail to respond to T cell-mediated immunotherapy and cancer cure rate of anti-PD-1 mAb is still limited. Therefore there is need to understand the molecular mechanisms of intrinsic and acquired resistance and identify new therapies to overcome the resistance and/or increase the cure rate of anti-PD-1 mAb.

In addition to aberrant activation in cancer cells, the PI3K pathway plays both positive and negative roles in immune response. Therefore, the overall outcome of PI3K inhibition on anti-tumor immunity and the combination strategy with aPD-1 and other immune checkpoint inhibitors (ICIs) are difficult to predict and should be carefully investigated.

In this invention, PI3K inhibition alone and in combination with anti-PD-1 mAb were evaluated in a set of syngeneic tumor models non-responding (no tumor regression) or insensitive to ICIs. We found that intermittent treatment compound A produced better anti-tumor efficacy, increased intratumoral CD8+ T cell vs Treg (regulatory T cell) ratio compared to each monotherapies. In addition, treatment of compound A with subsequent combination of anti-PD-1 mAb induced complete tumor regression in 50-100% of animals bearing $T_{reg}^{high}$ A20 lymphoma tumor compared to 0% response in the monotherapy groups. Synergistic combination was also demonstrated in CT26 colorectal cancer models. Of note, no tumor growth was observed in a re-challenge study conducted 3 months post complete tumor regression in the combination group of the CT26 model, indicating that tumor specific memory T cells were generated to prevent tumor recurrence. Analysis of tumor infiltrating leukocytes revealed significant reductions in $T_{reg}$ but increases in CD8+ T cell. Taken together, combination of intermittently dosed PI3K inhibitor copanlisib with ICIs therefore might be a promising strategy to overcome the resistance induced by intratumoral oncogenic signaling and an immune suppressive tumor microenvironment.

For detailed overviews of the PI3K signaling pathway, PI3K inhibitors, and ongoing clinical trials, we refer the reader to recent reviews (1-4, 7).

As described in the present invention, 2-amino-N-[7-methoxy-8-(3-morpholin-4-ylpropoxy)-2,3-dihydroimidazo[1,2-c]quinazolin-5-yl]pyrimidine-5-carboxamide dihydrochloride, (a highly selective pan-Class I PI3K inhibitor with predominant activity against PI3Kα and PI3Kδ) and anti-Programmed Cell Death Protein 1 (also referred to as "PD-1" or "CD279" (cluster of differentiation 279)) antibody (anti-PD-1 mAb) as defined herein, were investigated as combination in inhibiting cancers with altered activation PI3K pathway and/or PI3K activation induced modulation of immune response, which not only provide survival signaling to tumor cells but also cause impaired anti-tumor immunity and the resistance to the cancer immune therapies. The applicable cancer indications are, but not limited to, colorectal cancer, lung cancer, breast cancer, prostate cancer, bladder cancer, gastric cancer, head and neck cancer, liver cancer, brain cancer, melanoma, ovarian cancer, pancreatic cancer, kidney cancer, endometrial cancer, lymphoma, leukemia, etc. as single agent or in combination with immunocheckpoint blockers and/or other targeted or chemo therapies.

Unexpectedly, and this represents a basis of the present invention, when combinations of:
  component A: one or more 2,3-dihydroimidazo[1,2-c] quinazoline compounds of general formula (A1) or (A2), or a physiologically acceptable salt, solvate, hydrate or stereoisomer thereof, as described and defined herein; with
  component B: anti-Programmed Cell Death Protein 1 (also referred to as "PD-1" or "CD279" (cluster of differentiation 279)) antibody (anti-PD-1 mAb), as described and defined herein;
were evaluated for the treatment of (but not limited to) colorectal cancer, lung cancer, breast cancer, prostate cancer, bladder cancer, gastric cancer, head and neck cancer, liver cancer, brain cancer, melanoma, ovarian cancer, pancreatic cancer, kidney cancer, endometrial cancer, lymphoma, leukemia, etc., synergistically increased anti-tumor activities were demonstrated with these combinations compared to each monotherapy, providing a fundamental rationale for the clinical combination therapy using PI3K inhibitors—anti-Programmed Cell Death Protein 1 (also referred to as "PD-1" or "CD279" (cluster of differentiation 279)) antobody (anti-PD-1 mAb).

To the Applicant's knowledge, no generic or specific disclosure or suggestion in the prior art is known that either combinations of:
component A: one or more 2,3-dihydroimidazo[1,2-c]quinazoline compounds of general formula (A1) or (A2) as defined herein, or a physiologically acceptable salt, solvate, hydrate or stereoisomer thereof;
component B: anti-Programmed Cell Death Protein 1 (also referred to as "PD-1" or "CD279" (cluster of differentiation 279)) antibody (anti-PD-1 mAb);
in which optionally either or both of said components A and B of any of the above-mentioned combinations are in the form of a pharmaceutical formulation which is ready for use to be administered simultaneously, concurrently, separately or sequentially, would be effective in the treatment or prophylaxis of cancer, particularly (but not limited to) colorectal cancer, lung cancer, breast cancer, prostate cancer, bladder cancer, gastric cancer, head and neck cancer, liver cancer, brain cancer, melanoma, ovarian cancer, endometrial cancer, pancreatic cancer, kidney cancer, lymphoma, leukemia, etc.

Based on the action of the testing compounds described in this invention, the combinations of the present invention as described and defined herein, show a beneficial effect in the treatment of cancer, particularly (but not limited to) colorectal cancer, lung cancer, breast cancer, prostate cancer, bladder cancer, gastric cancer, head and neck cancer, liver cancer, brain cancer, melanoma, ovarian cancer, endometrial cancer, pancreatic cancer, kidney cancer, lymphoma, leukemia, etc.

Accordingly, in accordance with a first aspect, the present invention relates to combinations of:
component A: one or more 2,3-dihydroimidazo[1,2-c]quinazoline compounds of general formula (A1) or (A2) as defined herein, or a physiologically acceptable salt, solvate, hydrate or stereoisomer thereof;
component B: anti-Programmed Cell Death Protein 1 (also referred to as "PD-1" or "CD279" (cluster of differentiation 279)) antibody (anti-PD-1 mAb);

in which optionally either or both of said components A and B) of any of the above-mentioned combinations are in the form of a pharmaceutical formulation which is ready for use to be administered simultaneously, concurrently, separately or sequentially. The components may be administered independently of one another by the oral, intravenous, topical, local installations, intraperitoneal or nasal route.

In accordance with a second aspect, of the present invention relates to the use of any of such combinations as described supra for the preparation of a medicament for the treatment or prophylaxis of a cancer, particularly (but not limited to) colorectal cancer, lung cancer, breast cancer, prostate cancer, bladder cancer, gastric cancer, head and neck cancer, liver cancer, brain cancer, melanoma, ovarian cancer, pancreatic cancer, kidney cancer, endometrial cancer, lymphoma, leukemia, etc.

Further, in accordance with a third aspect, the present invention relates to a kit comprising a combination of:
component A: one or more 2,3-dihydroimidazo[1,2-c]quinazoline compounds of general formula (A1) or (A2) as defined herein, or a physiologically acceptable salt, solvate, hydrate or stereoisomer thereof;
component B: anti-Programmed Cell Death Protein 1 (also referred to as "PD-1" or "CD279" (cluster of differentiation 279)) antibody (anti-PD-1 mAb);
in which optionally either or both of components A and B in any of the above-mentioned combinations are in the form of a pharmaceutical formulation which is ready for use to be administered simultaneously, concurrently, separately or sequentially. The components may be administered independently of one another by the oral, intravenous, topical, local installations, intraperitoneal or nasal route.

In an embodiment of the third aspect, the present invention relates to a kit wherein:
said component A is 2-amino-N-[7-methoxy-8-(3-morpholin-4-ylpropoxy)-2,3-dihydroimidazo[1,2-c]quinazolin-5-yl]pyrimidine-5-carboxamide, or 2-amino-N-[7-methoxy-8-(3-morpholin-4-ylpropoxy)-2,3-dihydroimidazo[1,2-c]quinazolin-5-yl]pyrimidine-5-carboxamide dihydrochloride,
and
said anti-Programmed Cell Death Protein 1 (also referred to as "PD-1" or "CD279" (cluster of differentiation 279)) antibody (anti-PD-1 mAb) is pembrolizumab, nivolumab, pidilizumab, or tislelizumab.

In an embodiment of the third aspect, the present invention relates to a kit wherein:
said component A is 2-amino-N-[7-methoxy-8-(3-morpholin-4-ylpropoxy)-2,3-dihydroimidazo[1,2-c]quinazolin-5-yl]pyrimidine-5-carboxamide dihydrochloride,
and
said component B is anti-Programmed Cell Death Protein 1 (also referred to as "PD-1" or "CD279" (cluster of differentiation 279)) antibody (anti-PD-1 mAb).

In an embodiment of the third aspect, the present invention relates to a kit wherein:
said component A is 2-amino-N-[7-methoxy-8-(3-morpholin-4-ylpropoxy)-2,3-dihydroimidazo[1,2-c]quinazolin-5-yl]pyrimidine-5-carboxamide dihydrochloride,
and
said anti-Programmed Cell Death Protein 1 (also referred to as "PD-1" or "CD279" (cluster of differentiation 279)) antibody (anti-PD-1 mAb) is pembrolizumab.

In an embodiment of the third aspect, the present invention relates to a kit wherein:
said component A is 2-amino-N-[7-methoxy-8-(3-morpholin-4-ylpropoxy)-2,3-dihydroimidazo[1,2-c]quinazolin-5-yl]pyrimidine-5-carboxamide dihydrochloride,
and
said anti-Programmed Cell Death Protein 1 (also referred to as "PD-1" or "CD279" (cluster of differentiation 279)) antibody (anti-PD-1 mAb) is nivolumab.

BRIEF DESCRIPTION OF THE DRAWINGS

FIG. 2B is a table that shows the anti-tumor efficacy in the CT26 colorectal cancer model treated with Cpd A and/or Cpd B.

DETAILED DESCRIPTION OF THE INVENTION

Figures 1A, 1B:
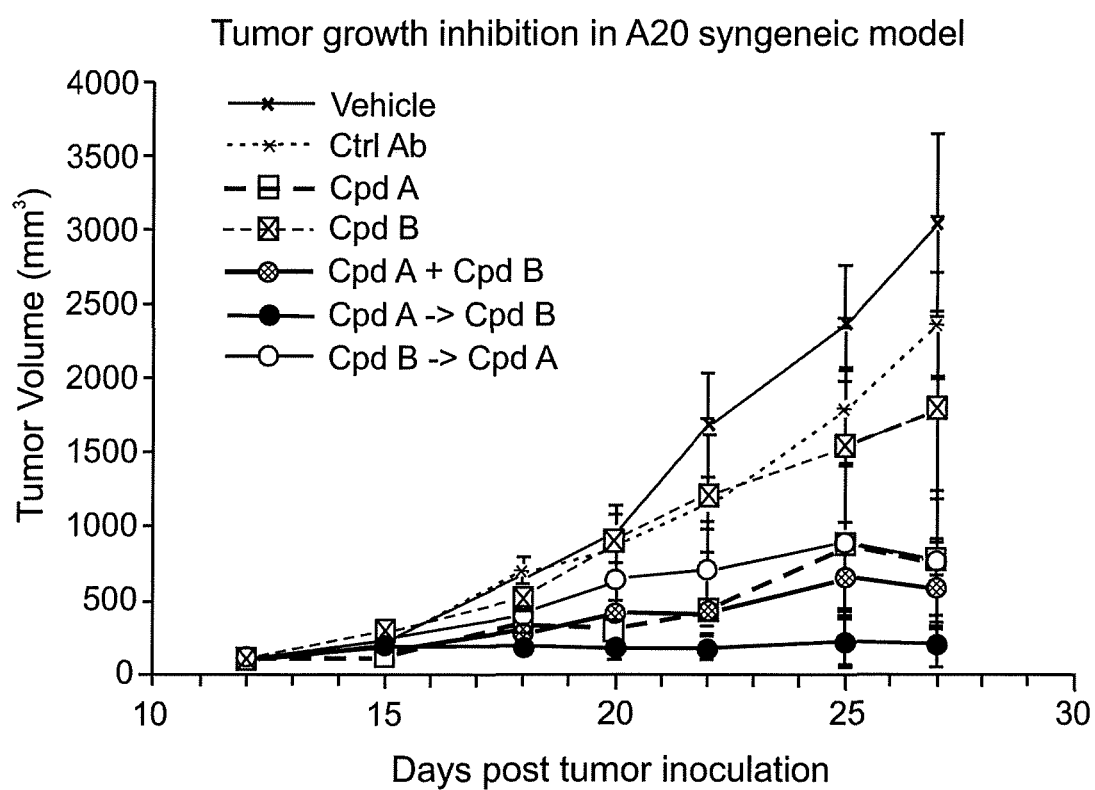
FIG. 1A is a table that shows 3 different combination dosing schedules during each 1-week treatment cycle for administration of Compound A and Compound B to a DLBCL syngeneic A20 xenograft mouse model.
FIG. 1B is a graph that shows tumor growth inhibition in the A20 syngeneic model.

In accordance with an embodiment of the above-mentioned aspects of the present invention, said combinations are of:
component A: which is one or more 2,3-dihydroimidazo[1,2-c]quinazoline compounds of general formula (A1):

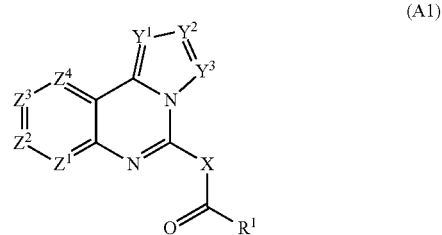

(A1)

wherein
X represents $CR^5R^6$ or NH;
$Y^1$ represents $CR^3$ or N;
Chemical bond between $Y^2 = Y^3$ represents a single bond or double bond, with the proviso that when the $Y^2 = Y^3$ represents a double bond, $Y^2$ and $Y^3$ independently represent $CR^4$ or N, and when $Y^2 = Y^3$ represents a single bond, $Y^2$ and $Y^3$ independently represent $CR^3R^4$ or $NR^4$;

$Z^1$, $Z^2$, $Z^3$ and $Z^4$ independently represent CH, $CR^2$ or N;

$R^1$ represents aryl optionally having 1 to 3 substituents selected from $R^{11}$, $C_{3-8}$ cycloalkyl optionally having 1 to 3 substituents selected from $R^{11}$, $C_{1-6}$ alkyl optionally substituted by aryl, heteroaryl, $C_{1-6}$ alkoxyaryl, aryloxy, heteroaryloxy or one or more halogen, $C_{1-6}$ alkoxy optionally substituted by carboxy, aryl, heteroaryl, $C_{1-6}$ alkoxyaryl, aryloxy, heteroaryloxy or one or more halogen, or a 3 to 15 membered mono- or bi-cyclic heterocyclic ring that is saturated or unsaturated, and contains 1 to 3 heteroatoms selected from the group consisting of N, O and S, and optionally having 1 to 3 substituents selected from $R^{11}$ wherein $R^{11}$ represents halogen, nitro, hydroxy, cyano, carboxy, amino, N-($C_{1-6}$alkyl)amino, N-(hydroxy$C_{1-6}$alkyl)amino, N,N-di($C_{1-6}$alkyl)amino, N-($C_{1-6}$acyl)amino, N-(formyl)-N-($C_{1-6}$alkyl)amino, N-($C_{1-6}$alkanesulfonyl)amino, N-(carboxy$C_{1-6}$alkyl)-N-($C_{1-6}$alkyl)amino, N-($C_{1-6}$alkoxycabonyl)amino, N-[N,N-di($C_{1-6}$alkyl)amino methylene]amino, N-[N,N-di($C_{1-6}$alkyl)amino ($C_{1-6}$ alkyl)methylene]amino, N-[N,N-di($C_{1-6}$alkyl)amino $C_{2-6}$alkenyl]amino, aminocarbonyl, N-($C_{1-6}$alkyl)aminocarbonyl, N,N-di($C_{1-6}$alkyl)aminocarbonyl, $C_{3-8}$cycloalkyl, $C_{1-6}$ alkylthio, $C_{1-6}$alkanesulfonyl, sulfamoyl, $C_{1-6}$alkoxycarbonyl, N-arylamino wherein said aryl moiety is optionally having 1 to 3 substituents selected from $R^{101}$, N-(aryl $C_{1-6}$alkyl)amino wherein said aryl moiety is optionally having 1 to 3 substituents selected from $R^{101}$, aryl $C_{1-6}$alkoxycarbonyl wherein said aryl moiety is optionally having 1 to 3 substituents selected from $R^{101}$, $C_{1-6}$alkyl optionally substituted by mono-, di- or tri-halogen, amino, N-($C_{1-6}$alkyl)amino or N,N-di($C_{1-6}$alkyl)amino, $C_{1-6}$alkoxy optionally substituted by mono-, di- or tri-halogen, N-($C_{1-6}$alkyl)sulfonamide, or N-(aryl)sulfonamide, or a 5 to 7 membered saturated or unsaturated ring having 1 to 3 heteroatoms selected from the group consisting of O, S and N, and optionally having 1 to 3 substituents selected from $R^{101}$ wherein $R^{101}$ represents halogen, carboxy, amino, N-($C_{1-6}$ alkyl)amino, N,N-di($C_{1-6}$alkyl)amino, aminocarbonyl, N-($C_{1-6}$alkyl)aminocarbonyl, N,N-di($C_{1-6}$alkyl)aminocarbonyl, pyridyl, $C_{1-6}$ alkyl optionally substituted by cyano or mono- di- or tri-halogen, or $C_{1-6}$alkoxy optionally substituted by cyano, carboxy, amino, N-($C_{1-6}$ alkyl)amino, N,N-di($C_{1-6}$alkyl)amino, aminocarbonyl, N-($C_{1-6}$alkyl)aminocarbonyl, N,N-di($C_{1-6}$alkyl)aminocarbonyl or mono-, di- or tri-halogen;

$R^2$ represents hydroxy, halogen, nitro, cyano, amino, N-($C_{1-6}$alkyl)amino, N,N-di($C_{1-6}$alkyl)amino, N-(hydroxy$C_{1-6}$alkyl)amino, N-(hydroxy$C_{1-6}$alkyl)-N-($C_{1-6}$alkyl)amino, $C_{1-6}$ acyloxy, amino$C_{1-6}$ acyloxy, $C_{2-6}$alkenyl, aryl, a 5-7 membered saturated or unsaturated heterocyclic ring having 1 to 3 heteroatoms selected from the group consisting O, S and N, and optionally substituted by hydroxy, $C_{1-6}$ alkyl, $C_{1-6}$ alkoxy, oxo, amino, amino $C_{1-6}$alkyl, N-($C_{1-6}$alkyl)amino, N,N-di($C_{1-6}$alkyl)amino, N-($C_{1-6}$ acyl)amino, N-($C_{1-6}$alkyl)carbonylamino, phenyl, phenyl $C_{1-6}$ alkyl, carboxy, $C_{1-6}$alkoxycarbonyl, aminocarbonyl, N-($C_{1-6}$alkyl)aminocarbonyl, or N,N-di($C_{1-6}$alkyl)amino,

—C(O)—$R^{20}$ wherein $R^{20}$ represents $C_{1-6}$ alkyl, $C_{1-6}$ alkoxy, amino, N-($C_{1-6}$alkyl)amino, N,N-di($C_{1-6}$alkyl)amino, N-($C_{1-6}$ acyl)amino, or a 5-7 membered saturated or unsaturated heterocyclic ring having 1 to 3 heteroatoms selected from the group consisting O, S and N, and optionally substituted by $C_{1-6}$ alkyl, $C_{1-6}$ alkoxy, oxo, amino, N-($C_{1-6}$alkyl)amino, N,N-di($C_{1-6}$alkyl)amino, N-($C_{2-6}$ acyl)amino, phenyl, or benzyl, $C_{1-6}$ alkyl optionally substituted by $R^{21}$ or $C_{1-6}$ alkoxy optionally substituted by $R^{21}$ wherein $R^{21}$ represents cyano, mono-, di or tri-halogen, hydroxy, amino, N-($C_{1-6}$alkyl)amino, N,N-di($C_{1-6}$alkyl)amino, N-(hydroxy$C_{1-6}$ alkyl)amino, N-(halophenyl$C_{1-6}$ alkyl)amino, amino $C_{2-6}$ alkylenyl, $C_{1-6}$ alkoxy, hydroxy$C_{1-6}$ alkoxy, —C(O)—$R^{201}$, —NHC(O)—$R^{201}$, $C_{3-8}$cycloalkyl, isoindolino, phthalimidyl, 2-oxo-1,3-oxazolidinyl, aryl or a 5 or 6 membered saturated or unsaturated heterocyclic ring having 1 to 4 heteroatoms selected from the group consisting O, S and N optionally substituted by hydroxy, $C_{1-6}$ alkyl, $C_{1-6}$ alkoxy, $C_{1-6}$ alkoxycarbonyl, hydroxy$C_{1-6}$ alkoxy, oxo, amino, amino$C_{1-6}$alkyl, N-($C_{1-6}$alkyl)amino, N,N-di($C_{1-6}$alkyl)amino, N-($C_{1-6}$ acyl)amino, or benzyl, wherein $R^{201}$ K represents hydroxy, amino, N-($C_{1-6}$alkyl)amino, N,N-di($C_{1-6}$alkyl)amino, N-(halophenyl$C_{1-6}$ alkyl)amino, $C_{1-6}$alkyl, amino$C_{1-6}$ alkyl, amino$C_{1-6}$ alkylenyl, $C_{1-6}$ alkoxy, a 5 or 6 membered saturated or unsaturated heterocyclic ring having 1 to 4 heteroatoms selected from the group consisting O, S and N optionally substituted by hydroxy, $C_{1-6}$ alkyl, $C_{1-6}$ alkoxy, $C_{1-6}$alkoxycarbonyl, hydroxy$C_{1-6}$ alkoxy, oxo, amino, N-($C_{1-6}$alkyl)amino, N,N-di($C_{1-6}$alkyl)amino, N-($C_{1-6}$acyl)amino or benzyl;

$R^3$ represents hydrogen, halogen, aminocarbonyl, or $C_{1-6}$ alkyl optionally substituted by aryl $C_{1-6}$ alkoxy or mono-, di- or tri-halogen;

$R^4$ represents hydrogen or $C_{1-6}$ alkyl;

$R^5$ represents hydrogen or $C_{1-6}$ alkyl; and $R^6$ represents halogen, hydrogen or $C_{1-6}$ alkyl;

or a physiologically acceptable salt, solvate, hydrate or stereoisomer thereof;

said compounds are published as compounds of general formulae I, I-a, and I-b in International patent application PCT/EP2003/010377, published as WO 04/029055 A1 on Apr. 8, 2004, which is incorporated herein by reference in its entirety. In WO 04/029055, said compounds of general formula I, I-a and I-b are described on pp. 6 et seq., they may be synthesized according to the methods given therein on pp. 26 et seq., and are exemplified as specific compound Examples 1-1 to 1-210 on pp. 47 to 106, specific compound Examples 2-1 to 2-368 on pp. 107 to 204, specific compound Examples 3-1 to 3-2 on pp. 205 to 207, and as specific compound Examples 4-1 to 4-2 on pp. 208 to 210, therein.

Such a compound, 2-amino-N-[7-methoxy-8-(3-morpholin-4-ylpropoxy)-2,3-dihydroimid-azo[1,2-c]quinazolin-5-yl]pyrimidine-5-carboxamide dihydrochloride, (which is hereinafter referred to as "compound A" or "cpd. A") is published in international patent application PCT/EP2012/055600, published as WO 2012/136553 on Oct. 11, 2012, (which is incorporated herein by reference in its entirety), as the compound of Examples 1 and 2: 2-amino-N-[7-methoxy-8-(3-morpholin-4-ylpropoxy)-2,3-dihydroimidazo[1,2-c]quinazolin-5-yl]pyrimidine-5-carboxamide dinydrochloride: it may be synthesized according to the methods given in said Examples 1 and 2.

Said component A may be in the form of a pharmaceutical formulation which is ready for use to be administered simultaneously, concurrently, separately or sequentially. The components may be administered independnently of one another by the oral, intravenous, topical, local installations, intraperitoneal or nasal route.

In accordance with another embodiment of the above-mentioned aspects of the present invention, said combinations are of:
component A: which is one or more 2,3-dihydroimidazo[1,2-c]quinazoline compounds of general formula (A1), supra, which is selected from the list consisting of specific compound Examples 1-1 to 1-210 on pp. 47 to 106, specific compound Examples 2-1 to 2-368 on pp. 107 to 204, specific compound Examples 3-1 to 3-2 on pp. 205 to 207, and specific compound Examples 4-1 to 4-2 on pp. 208 to 210, of in International patent application PCT/EP2003/010377, published as WO 04/029055 A1 on Apr. 8, 2004, which is incorporated herein by reference in its entirety;
or a physiologically acceptable salt, solvate, hydrate or stereoisomer thereof.

Such a component A may be: 2-amino-N-[7-methoxy-8-(3-morpholin-4-ylpropoxy) -2,3-dihydroimid-azo[1,2-c]quinazolin-5-yl]pyrimidine-5-carboxamide dihydrochloride, (which is hereinafter referred to as "compound A" or "cpd. A") is published in international patent application PCT/EP2012/055600, published as WO 2012/136553 on Oct. 11, 2012, (which is incorporated herein by reference in its entirety), as the compound of Examples 1 and 2: 2-amino-N-[7-methoxy-8-(3-morpholin-4-ylpropoxy) -2,3-dihydroimidazo[1,2-c]quinazolin-5-yl]pyrimidine-5-carboxamide dihydrochloride: it may be synthesized according to the methods given in said Examples 1 and 2.

Said component A may be in the form of a pharmaceutical formulation which is ready for use to be administered simultaneously, concurrently, separately or sequentially. The components may be administered independnently of one another by the oral, intravenous, topical, local installations, intraperitoneal or nasal route.

As mentioned supra, said specific compound Examples may be synthesized according to the methods given in WO 04/029055 A1 on pp. 26 et seq.

As mentioned supra, 2-amino-N-[7-methoxy-8-(3-morpholin-4-ylpropoxy) -2,3-dihydroimid-azo[1,2-c]quinazolin-5-yl]pyrimidine-5-carboxamide dihydrochloride, (which is hereinafter referred to as "compound A" or "cpd. A") may be synthesized as described in Examples 1 and 2 of international patent application PCT/EP2012/055600, published as WO 2012/136553 on Oct. 11, 2012, (which is incorporated herein by reference in its entirety).

In accordance with another embodiment of the above-mentioned aspects of the present invention, said combinations are of:
component A: which is one or more 2,3-dihydroimidazo[1,2-c]quinazoline compounds of general formula (A2):

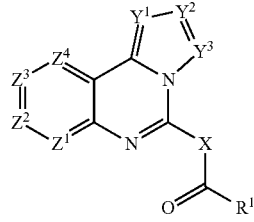

(A2)

in which:
X represents $CR^5R^6$ or NH;
$Y^1$ represents $CR^3$ or N;
the chemical bond between $Y^2 \!\!=\!\! Y^3$ represents a single bond or double bond,
with the proviso that when the $Y^2 \!\!=\!\! Y^3$ represents a double bond, $Y^2$ and $Y^3$ independently represent $CR^4$ or N, and when $Y^2 \!\!=\!\! Y^3$ represents a single bond, $Y^2$ and $Y^3$ independently represent $CR^3R^4$ or $NR^4$;
$Z^1$, $Z^2$, $Z^3$ and $Z^4$ independently represent CH, $CR^2$ or N;
$R^1$ represents aryl optionally having 1 to 3 substituents selected from $R^{11}$, $C_{3-8}$ cycloalkyl optionally having 1 to 3 substituents selected from $R^{11}$,
$C_{1-6}$ alkyl optionally substituted by aryl, heteroaryl, $C_{1-6}$ alkoxyaryl, aryloxy, heteroaryloxy or one or more halogen,
$C_{1-6}$ alkoxy optionally substituted by carboxy, aryl, heteroaryl, $C_{1-6}$ alkoxyaryl, aryloxy, heteroaryloxy or one or more halogen,
or
a 3 to 15 membered mono- or bi-cyclic heterocyclic ring that is saturated or unsaturated, optionally having 1 to 3 substituents selected from $R^{11}$, and contains 1 to 3 heteroatoms selected from the group consisting of N, O and S,
wherein
$R^{11}$ represents halogen, nitro, hydroxy, cyano, carboxy, amino, N-($C_{1-6}$alkyl)amino, N-(hydroxy$C_{1-6}$alkyl)amino, N,N-di($C_{1-6}$alkyl)amino, N-($C_{1-6}$acyl)amino, N-(formyl)-N-($C_{1-6}$alkyl)amino, N-($C_{1-6}$alkanesulfonyl)amino, N-(carboxy$C_{1-6}$alkyl)-N-($C_{1-6}$alkyl)amino, N-($C_{1-6}$alkoxycabonyl)amino, N-[N,N-di($C_{1-6}$alkyl) amino methylene]amino, N-[N,N-di($C_{1-6}$alkyl)amino ($C_{1-6}$alkyl)methylene]amino, N-[N,N-di($C_{1-6}$alkyl)amino $C_{2-6}$alkenyl]amino, aminocarbonyl, N-($C_{1-6}$alkyl)aminocarbonyl, N,N-di($C_{1-6}$alkyl)aminocarbonyl, $C_{3-8}$cycloalkyl, $C_{1-6}$ alkylthio, $C_{1-6}$alkanesulfonyl, sulfamoyl, $C_{1-6}$alkoxycarbonyl, N-arylamino wherein said aryl moiety is optionally having 1 to 3 substituents selected from $R^{101}$, N-(aryl $C_{1-6}$alkyl)amino wherein said aryl moiety is optionally having 1 to 3 substituents selected from $R^{101}$, aryl $C_{1-6}$alkoxycarbonyl wherein said aryl moiety is optionally having Ito 3 substituents selected from $R^{101}$,
$C_{1-6}$alkyl optionally substituted by mono-, di- or tri-halogen, amino, N-($C_{1-6}$alkyl)amino or N,N-di($C_{1-6}$alkyl)amino,
$C_{1-6}$alkoxy optionally substituted by mono-, di- or tri-halogen, N-($C_{1-6}$alkyl)sulfonamide, or N-(aryl)sulfonamide,
or
a 5 to 7 membered saturated or unsaturated ring having 1 to 3 heteroatoms selected from the group consisting of O, S and N, and optionally having 1 to 3 substituents selected from $R^{101}$ wherein $R^{101}$ represents halogen, carboxy, amino, N-($C_{2-6}$ alkyl) amino, N,N-di($C_{1-6}$alkyl)amino, aminocarbonyl, N-($C_{1-6}$alkyl)aminocarbonyl, N,N-di($C_{1-6}$alkyl)aminocarbonyl, pyridyl, $C_{1-6}$ alkyl optionally substituted by cyano or mono- di- or tri-halogen, and $C_{1-6}$alkoxy optionally substituted by cyano, carboxy, amino, N-($C_{1-6}$ alkyl)amino, N,N-di($C_{1-6}$alkyl)amino, aminocarbonyl, N-($C_{1-6}$alkyl)aminocarbonyl, N,N-di($C_{1-6}$alkyl) aminocarbonyl or mono-, di- or tri-halogen;

$R^2$ represents hydroxy, halogen, nitro, cyano, amino, N-($C_{1-6}$alkyl)amino, N,N-di($C_{1-6}$alkyl)amino, N-(hydroxy$C_{1-6}$alkyl)amino, N-(hydroxy$C_{1-6}$alkyl)-N-($C_{1-6}$alkyl)amino, $C_{1-6}$ acyloxy, amino$C_{1-6}$acyloxy, $C_{2-6}$alkenyl, aryl, a 5-7 membered saturated or unsaturated heterocyclic ring having 1 to 3 heteroatoms selected from the group consisting O, S and N, and optionally substituted by hydroxy, $C_{1-6}$ alkyl, $C_{1-6}$ alkoxy, oxo, amino, amino $C_{1-6}$alkyl, N-($C_{1-6}$alkyl)amino, N,N-di($C_{1-6}$alkyl)amino, N-($C_{1-6}$ acyl)amino, N-($C_{1-6}$alkyl)carbonylamino, phenyl, phenyl $C_{1-6}$ alkyl, carboxy, $C_{1-6}$alkoxycarbonyl, aminocarbonyl, N-($C_{1-6}$alkyl)aminocarbonyl, or N,N-di($C_{1-6}$alkyl)amino, —C(O)—$R^{20}$ wherein $R^{20}$ represents $C_{1-6}$ alkyl, $C_{1-6}$ alkoxy, amino, N-($C_{1-6}$alkyl) amino, N,N-di($C_{1-6}$alkyl)amino, N-($C_{1-6}$ acyl)amino, or a 5-7 membered saturated or unsaturated heterocyclic ring having 1 to 3 heteroatoms selected from the group consisting O, S and N, and optionally substituted by $C_{1-6}$ alkyl, $C_{1-6}$ alkoxy, oxo, amino, N-($C_{1-6}$alkyl)amino, N,N-di($C_{1-6}$alkyl)amino, N-($C_{1-6}$ acyl)amino, phenyl, or benzyl, $C_{1-6}$ alkyl optionally substituted by $R^{21}$, or $C_{1-6}$ alkoxy optionally substituted by $R^{21}$, wherein $R^{21}$ represents cyano, mono-, di or tri-halogen, hydroxy, amino, N-($C_{1-6}$alkyl)amino, N,N-di($C_{1-6}$alkyl)amino, N-(hydroxy$C_{1-6}$ alkyl) amino, N-(halophenyl$C_{1-6}$ alkyl) amino, amino $C_{2-6}$ alkylenyl, $C_{1-6}$ alkoxy, hydroxy$C_{1-6}$ alkoxy, —C(O)—$R^{201}$, —NHC(O)—$R^{201}$, $C_{3-8}$cycloalkyl, isoindolino, phthalimidyl, 2-oxo-1,3-oxazolidinyl, aryl or a 5 or 6 membered saturated or unsaturated heterocyclic ring having 1 to 4 heteroatoms selected from the group consisting O, S and N, and optionally substituted by hydroxy, $C_{1-6}$ alkyl, $C_{1-6}$ alkoxy, $C_{1-6}$ alkoxycarbonyl, hydroxy$C_{1-6}$ alkoxy, oxo, amino, amino$C_{1-6}$alkyl, N-($C_{1-6}$alkyl)amino, N,N-di($C_{1-6}$alkyl)amino, N-($C_{1-6}$acyl)amino, or benzyl, wherein $R^{201}$ K represents hydroxy, amino, N-($C_{1-6}$alkyl)amino, N,N-di($C_{1-6}$alkyl)amino, N-(halophenyl$C_{1-6}$ alkyl)amino, $C_{1-6}$alkyl, amino$C_{1-6}$ alkyl, amino$C_{2-6}$ alkylenyl, $C_{1-6}$ alkoxy, a 5 or 6 membered saturated or unsaturated heterocyclic ring having 1 to 4 heteroatoms selected from the group consisting O, S and N, and optionally substituted by hydroxy, $C_{1-6}$ alkyl, $C_{1-6}$ alkoxy, $C_{1-6}$ alkoxycarbonyl, hydroxy$C_{1-6}$ alkoxy, oxo, amino, N-($C_{1-6}$alkyl)amino, N,N-di($C_{1-6}$alkyl)amino, N-($C_{1-6}$ acyl)amino or benzyl;

$R^3$ represents hydrogen, halogen, aminocarbonyl, or $C_{1-6}$ alkyl optionally substituted by aryl $C_{1-6}$ alkoxy or mono-, di- or tri-halogen;

$R^4$ represents hydrogen or $C_{1-6}$ alkyl;

$R^5$ represents hydrogen or $C_{1-6}$ alkyl; and $R^6$ represents halogen, hydrogen or $C_{1-6}$ alkyl;

or a physiologically acceptable salt, solvate, hydrate or stereoisomer thereof;

said compounds are published as compounds of general formulae I, Ia, Ib, Ic, Id and Ie in International patent application PCT/US2007/024985, published as WO 2008/070150 A1 on Jun. 12, 2008, which is incorporated herein by reference in its entirety. In WO 2008/070150, said compounds of general formula I, Ia, Ib, Ic, Id and Ie are described on pp. 9 et seq., they may be synthesized according to the methods given therein on pp. 42, et seq., and are exemplified as specific compound Examples 1 to 103 therein on pp. 65 to 101. Biological test data for certain of said compounds are given therein on pp. 101 to 107.

2-amino-N-[7-methoxy-8-(3-morpholin-4-ylpropoxy)-2,3-dihydroimid-azo[1,2-c]quinazolin-5-yl]pyrimidine-5-carboxamide dihydrochloride, (which is hereinafter referred to as "compound A" or "cpd. A") is published in international patent application PCT/EP2012/055600, published as WO 2012/136553 on Oct. 11, 2012, (which is incorporated herein by reference in its entirety), as the compound of Examples 1 and 2: 2-amino-N-[7-methoxy-8-(3-morpholin-4-ylpropoxy)-2,3-dihydroimidazo[1,2-c]quinazolin-5-yl]pyrimidine-5-carboxamide dinydrochloride: it may be synthesized according to the methods given in said Examples 1 and 2.

The definitions used in relation to the structure (A) in this text are as follows:

The term 'alkyl' refers to a straight or branched hydrocarbon chain radical consisting solely of carbon and hydrogen atoms, containing solely of carbon and hydrogen atoms, containing no unsaturation, having from one to eight carbon atoms, and which is attached to the rest of the molecule by a single bond, such as illustratively, methyl, ethyl, n-propyl 1-methylethyl (isopropyl), n-butyl, n-pentyl, and 1,1-dimethylethyl (t-butyl).

The term "alkenyl " refers to an aliphatic hydrocarbon group containing a carbon-carbon double bond and which may be a straight or branched or branched chain having about 2 to about 10 carbon atoms, e.g., ethenyl, 1-propenyl, 2-propenyl (allyl), iso-propenyl, 2-methyl-1-propenyl, 1-butenyl, 2-and butenyl.

The term "alkynyl" refers to a straight or branched chain hydrocarbonyl radicals having at least one carbon-carbon triple bond, and having in the range of about 2 up to 12 carbon atoms (with radicals having in the range of about 2 up to 10 carbon atoms presently being preferred) e.g., ethynyl.

The term "alkoxy" denotes an alkyl group as defined herein attached via oxygen linkage to the rest of the molecule. Representative examples of those groups are methoxy and ethoxy.

The term "alkoxyakyl" denotes an alkoxy group as defined herein attached via oxygen linkage to an alkyl group which is then attached to the main structure at any carbon from alkyl group that results in the creation of a stable structure the rest of the molecule. Representative examples of those groups are —$CH_2OCH_3$ and —$CH_2OC_2H_5$.

The term "cycloalkyl" denotes a non-aromatic mono or multicyclic ring system of about 3 to 12 carbon atoms such as cyclopropyl, cyclobutyl, cyclopentyl, cyclohexyl and examples of multicyclic cycloalkyl groups include perhydronapththyl, adamantyl and norbornyl groups bridged cyclic group or sprirobicyclic groups e.g sprio (4,4) non-2-yl.

The term "cycloalkylalkyl" refers to cyclic ring-containing radicals containing in the range of about about 3 up to 8 carbon atoms directly attached to alkyl group which is then also attached to the main structure at any carbon from the alkyl group that results in the creation of a stable structure such as cyclopropylmethyl, cyclobuyylethyl, cyclopentylethyl.

The term "aryl" refers to aromatic radicals having in the range of 6 up to 14 carbon atoms such as phenyl, naphthyl, tetrahydronapthyl, indanyl, biphenyl.

The term "arylalkyl" refers to an aryl group as defined herein directly bonded to an alkyl group as defined herein which is then attached to the main structure at any carbon from alkyl group that results in the creation of a stable structure the rest of the molecule. e.g., —$CH_2C_6H_5$, —$C_2H_5C_6H_5$.

The term "heterocyclic ring" refers to a stable 3- to 15 membered ring radical which consists of carbon atoms and from one to five heteroatoms selected from the group consisting of nitrogen, phosphorus, oxygen and sulfur. For purposes of this invention, the heterocyclic ring radical may be a monocyclic, bicyclic or tricyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized; and the ring radical may be partially or fully saturated (i.e., heteroaromatic or heteroaryl aromatic). Examples of such heterocyclic ring radicals include, but are not limited to, azetidinyl, acridinyl, benzodioxolyl, benzodioxanyl, benzofurnyl, carbazolyl cinnolinyl dioxolanyl, indolizinyl, naphthyridinyl, perhydroazepinyl, phenazinyl, phenothiazinyl, phenoxazinyl, phthalazil, pyridyl, pteridinyl, purinyl, quinazolinyl, quinoxalinyl, quinolinyl, isoquinolinyl, tetrazoyl, imidazolyl tetrahydroisouinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazinyl, pyrimidinyl pyridazinyl, oxazolyl oxazolinyl oxasolidinyl, triazolyl, indanyl, isoxazolyl, isoxasolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl quinolyl, isoquinolyl, decahydroisoquinolyl, benzimidazolyl, thiadiazolyl, benzopyranyl, benzothiazolyl, benzooxazolyl, furyl, tetrahydrofurtyl, tetrahydropyranyl, thienyl, benzothienyl, thiamorpholinyl, thiamorpholinyl sulfoxide thiamorpholinyl sulfone, dioxaphospholanyl, oxadiazolyl, chromanyl, isochromanyl.

The term "heteroaryl" refers to heterocyclic ring radical as defined herein which are aromatic. The heteroaryl ring radical may be attached to the main structure at any heteroatom or carbon atom that results in the creation of a stable structure.

The heterocyclic ring radical may be attached to the main structure at any heteroatom or carbon atom that results in the creation of a stable structure.

The term "heteroarylalkyl" refers to heteroaryl ring radical as defined herein directly bonded to alkyl group. The heteroarylalkyl radical may be attached to the main structure at any carbon atom from alkyl group that results in the creation of a stable structure.

The term "heterocyclyl" refers to a heterocylic ring radical as defined herein. The heterocylyl ring radical may be attached to the main structure at any heteroatom or carbon atom that results in the creation of a stable structure.

The term "heterocyclylalkyl" refers to a heterocylic ring radical as defined herein directly bonded to alkyl group. The heterocyclylalkyl radical may be attached to the main structure at carbon atom in the alkyl group that results in the creation of a stable structure.

The term "carbonyl" refers to an oxygen atom bound to a carbon atom of the molecule by a double bond.

The term "halogen" refers to radicals of fluorine, chlorine, bromine and iodine.

Said component A may be in the form of a pharmaceutical formulation which is ready for use to be administered simultaneously, concurrently, separately or sequentially. The components may be administered independnently of one another by the oral, intravenous, topical, local installations, intraperitoneal or nasal route.

In accordance with another embodiment of the abovementioned aspects of the present invention, said combinations are of:

component A: which is one or more 2,3-dihydroimidazo[1,2-c]quinazoline compounds of general formula (A2), supra, which is selected from the list consisting of:

Example 1: N-[7-methoxy-8-(3-morpholin-4-ylpropoxy)-2,3-dihydroimidazo[1,2-c]quinazolin-5-yl]pyrimidine-5-carboxamide Example 2: N-(8-{3-[(2R,6S)-2,6-dimethylmorpholin-4-yl]propoxy}-7-methoxy-2,3-dihydroimidazo[1,2-c]quinazolin-5-yl)nicotinamide Example 3: N-(8-{3-[(2R,6S)-2,6-dimethylmorpholin-4-yl]propoxy}-7-methoxy-2,3-dihydroimidazo[1,2-c]quinazolin-5-yl)-2,4-dimethyl-1,3-thiazole-5-carboxamide Example 4: 2-amino-N-[7-methoxy-8-(3-morpholin-4-ylpropoxy)-2,3-dihydroimidazo[1,2-c]quinazolin-5-yl]-1,3-thiazole-5-carboxamide.

Example 5: 2-amino-N-[7-methoxy-8-(3-morpholin-4-ylpropoxy)-2,3-dihydroimidazo[1,2-c]quinazolin-5-yl]isonicotinamide Example 6: 2-amino-N-[7-methoxy-8-(3-morpholin-4-ylpropoxy)-2,3-dihydroimidazo[1,2-c]quinazolin-5-yl]-4-methyl-1,3-thiazole-5-carboxamide Example 7: 2-amino-N-[7-methoxy-8-(3-morpholin-4-ylpropoxy)-2,3-dihydroimidazo[1,2-c]quinazolin-5-yl]-4-propylpyrimidine-5-carboxamide Example 8: N-{8-[2-(4-ethylmorpholin-2-yl)ethoxy]-7-methoxy-2,3-dihydroimidazo[1,2-c]quinazolin-5-yl}nicotinamide Example 9: N-{8-[2-(dimethylamino)ethoxy]-7-methoxy-2,3-dihydroimidazo[1,2-c]quinazolin-5-yl}pyrimidine-5-carboxamide Example 10: N-(8-{3-[2-(hydroxymethyl)morpholin-4-yl]propoxy}-7-methoxy-2,3-dihydroimidazo[1,2-c]quinazolin-5-yl)nicotinamide Example 11: N-(8-{3-[2-(hydroxymethyl)morpholin-4-yl]propoxy}-7-methoxy-2,3-dihydroimidazo[1,2-c]quinazolin-5-yl)nicotinamide Example 12: N-{8-[3-(dimethylamino)propoxy]-7-methoxy-2,3-dihydroimidazo[1,2-c]quinazolin-5-yl}nicotinamide 1-oxide Example 13: 2-amino-N-[7-methoxy-8-(3-morpholin-4-ylpropoxy)-2,3-dihydroimidazo[1,2-c]quinazolin-5-yl]pyrimidine-5-carboxamide.

Example 14: N-[7-methoxy-8-(3-morpholin-4-ylpropoxy)-2,3-dihydroimidazo[1,2-c]quinazolin-5-yl]-6-(2-pyrrolidin-1-ylethyl)nicotinamide Example 15: 6-(cyclopentylamino)-N-[7-methoxy-8-(3-morpholin-4-ylpropoxy)-2,3-dihydroimidazo[1,2-c]quinazolin-5-yl]nicotinamide

| Example | Structure |
|---|---|
| 16 | 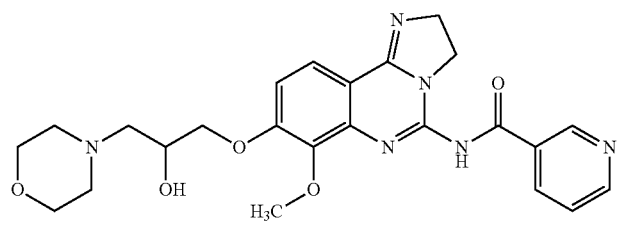 [SMILES: COc1c(OCC(O)CN2CCOCC2)ccc2c1N=C(NC(=O)c1cccnc1)N1CCN=C21] |
| 17 | 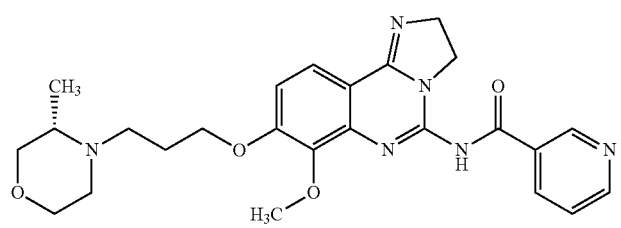 [SMILES: COc1c(OCCCN2CCOC[C@@H]2C)ccc2c1N=C(NC(=O)c1cccnc1)N1CCN=C21] |
| 18 | 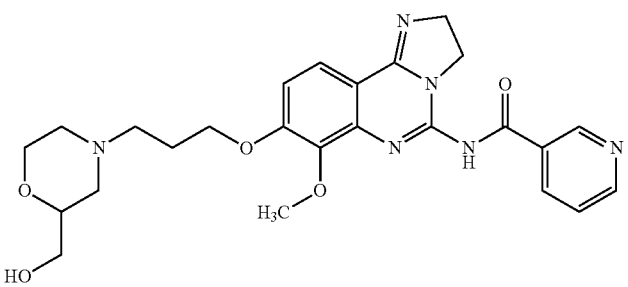 [SMILES: COc1c(OCCCN2CCOC(CO)C2)ccc2c1N=C(NC(=O)c1cccnc1)N1CCN=C21] |
| 19 | 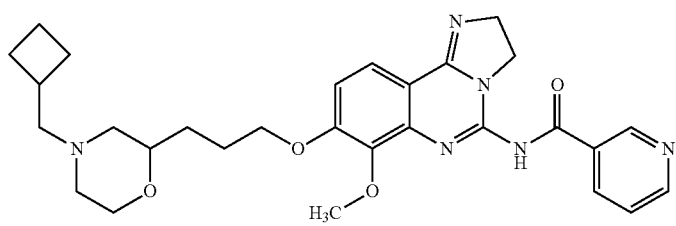 [SMILES: COc1c(OCCCC2CN(CC3CCC3)CCO2)ccc2c1N=C(NC(=O)c1cccnc1)N1CCN=C21] |
| 20 | 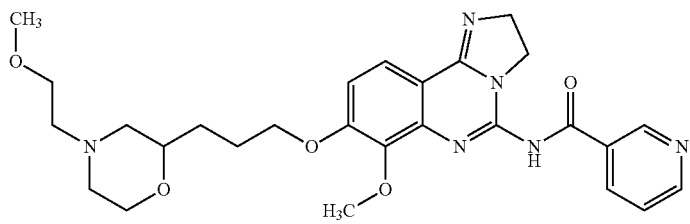 [SMILES: COCCN1CCOC(CCCOc2ccc3c(c2OC)N=C(NC(=O)c2cccnc2)N2CCN=C32)C1] |
| 21 | 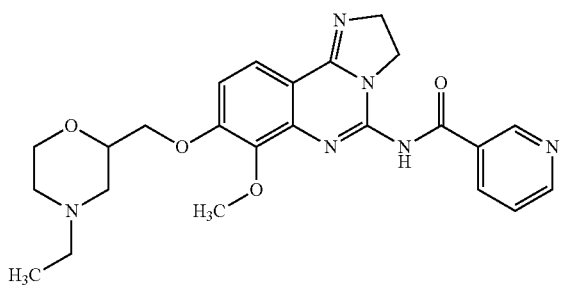 [SMILES: CCN1CCOC(COc2ccc3c(c2OC)N=C(NC(=O)c2cccnc2)N2CCN=C32)C1] |

-continued
| Example | Structure |
|---|---|
| 22 | 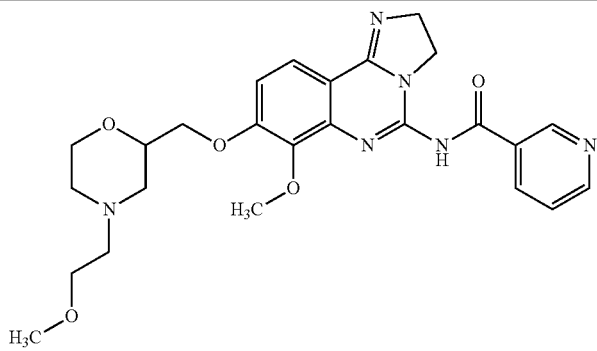 [SMILES: COCCN1CCOC(COc2ccc3c(c2OC)N=C(NC(=O)c2cccnc2)N2CCN=C32)C1] |
| 23 | 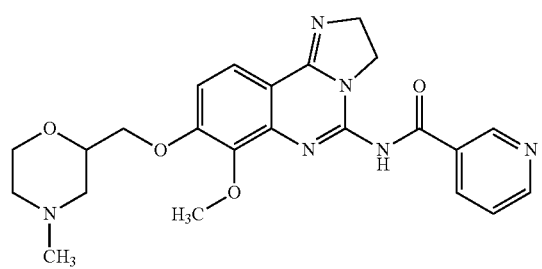 [SMILES: COc1c(OCC2CN(C)CCO2)ccc2c1N=C(NC(=O)c1cccnc1)N1CCN=C21] |
| 24 | 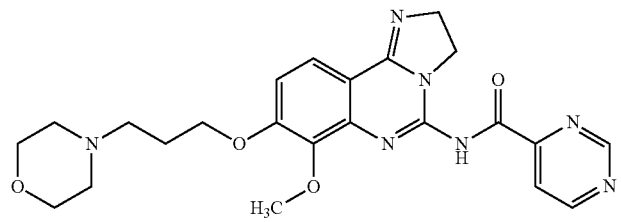 [SMILES: COc1c(OCCCN2CCOCC2)ccc2c1N=C(NC(=O)c1ccncn1)N1CCN=C21] |
| 25 | 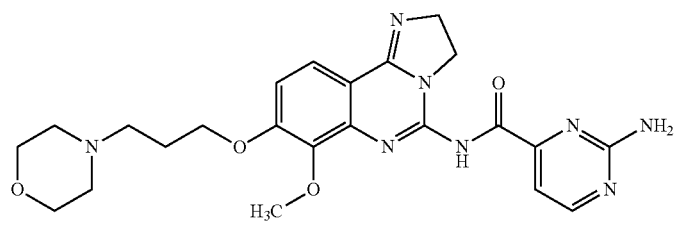 [SMILES: COc1c(OCCCN2CCOCC2)ccc2c1N=C(NC(=O)c1ccnc(N)n1)N1CCN=C21] |
| 26 | 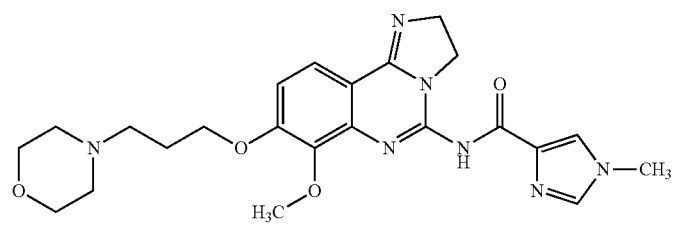 [SMILES: COc1c(OCCCN2CCOCC2)ccc2c1N=C(NC(=O)c1cn(C)cn1)N1CCN=C21] |
| 27 | 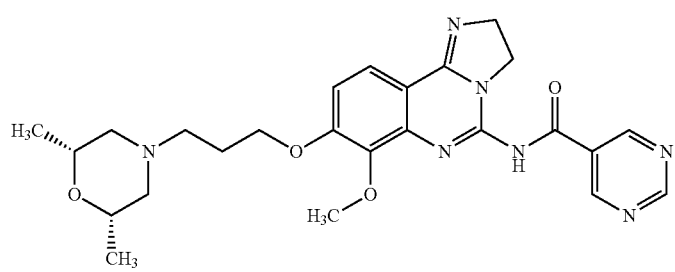 [SMILES: COc1c(OCCCN2C[C@@H](C)O[C@@H](C)C2)ccc2c1N=C(NC(=O)c1cncnc1)N1CCN=C21] |

-continued
| Example | Structure |
|---|---|
| 28 | 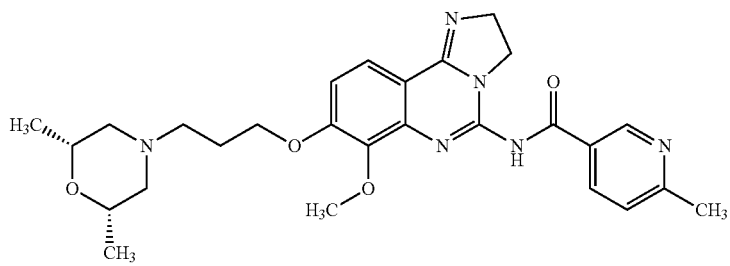 |
| 29 | 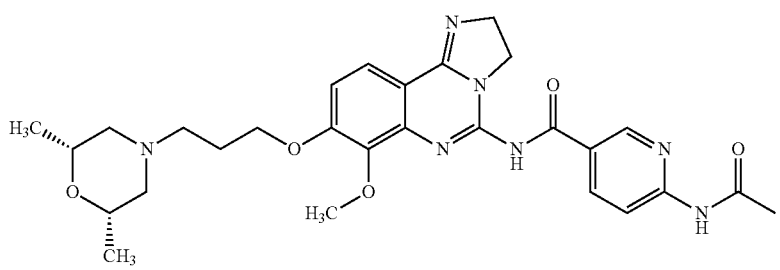 [SMILES: COc1c(OCCCN2C[C@@H](C)O[C@@H](C)C2)ccc2c1N=C(NC(=O)c1ccc(NC(C)=O)nc1)N1CCN=C21] |
| 30 | 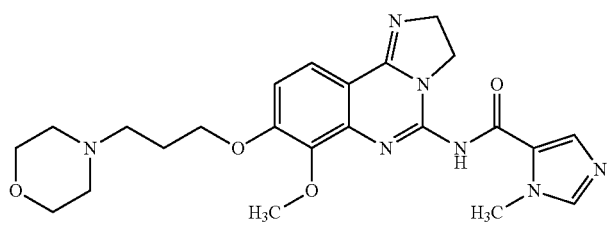 [SMILES: COc1c(OCCCN2CCOCC2)ccc2c1N=C(NC(=O)c1cncn1C)N1CCN=C21] |
| 31 | 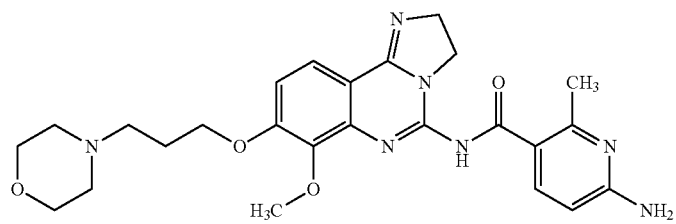 |
| 32 | 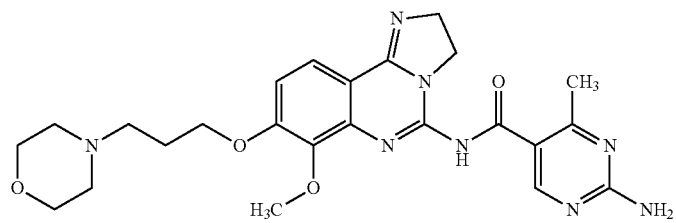 [SMILES: COc1c(OCCCN2CCOCC2)ccc2c1N=C(NC(=O)c1cnc(N)nc1C)N1CCN=C21] |
| 33 | 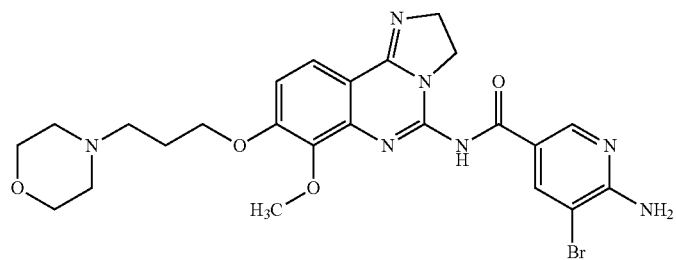 [SMILES: COc1c(OCCCN2CCOCC2)ccc2c1N=C(NC(=O)c1cnc(N)c(Br)c1)N1CCN=C21] |

| Example | Structure |
|---------|-----------|
| 34 | 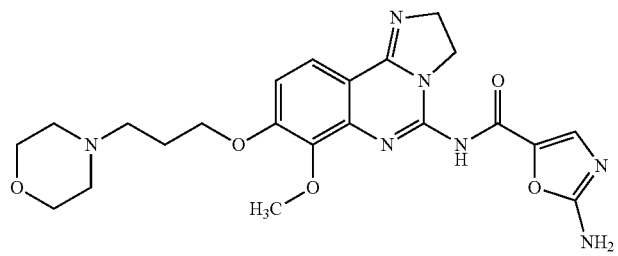 [SMILES: COc1c(OCCCN2CCOCC2)ccc2c1N=C(NC(=O)c1cnc(N)o1)N1CCN=C21] |
| 35 | 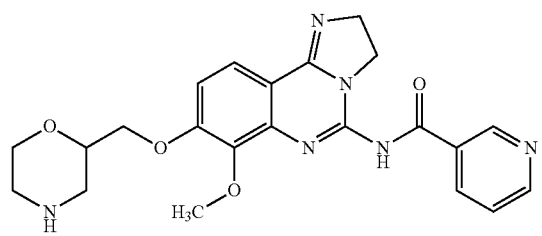 [SMILES: COc1c(OCC2CNCCO2)ccc2c1N=C(NC(=O)c1cccnc1)N1CCN=C21] |
| 36 | 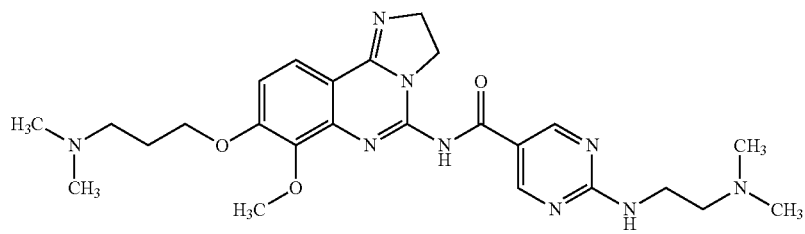 |
| 37 | 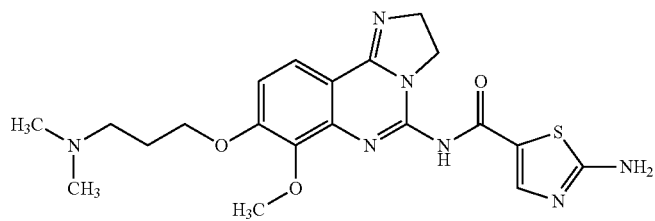 [SMILES: COc1c(OCCCN(C)C)ccc2c1N=C(NC(=O)c1cnc(N)s1)N1CCN=C21] |
| 38 | 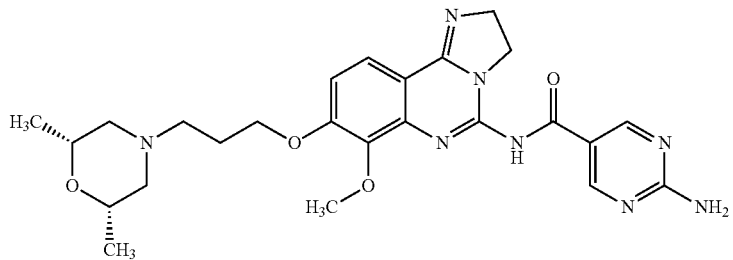 [SMILES: COc1c(OCCCN2C[C@@H](C)O[C@@H](C)C2)ccc2c1N=C(NC(=O)c1cnc(N)nc1)N1CCN=C21] |
| 39 | 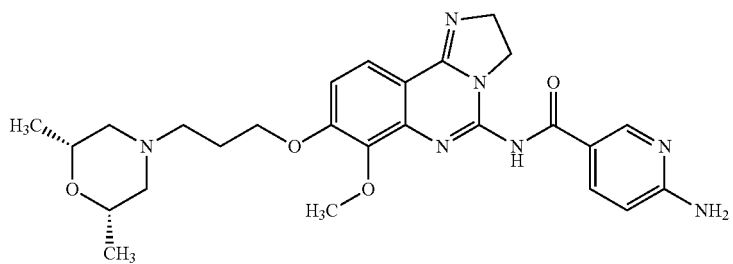 [SMILES: COc1c(OCCCN2C[C@@H](C)O[C@@H](C)C2)ccc2c1N=C(NC(=O)c1ccc(N)nc1)N1CCN=C21] |

| Example | Structure |
|---|---|
| 40 | 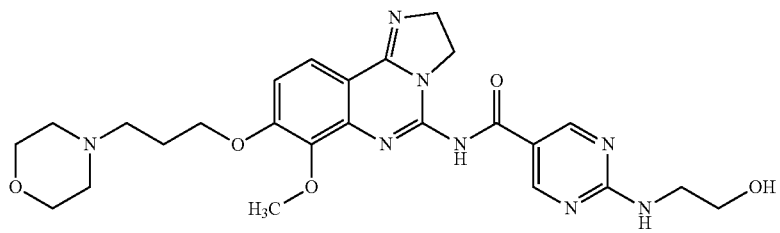 [SMILES: COc1c(OCCCN2CCOCC2)ccc2c1N=C(NC(=O)c1cnc(NCCO)nc1)N1CCN=C21] |
| 41 | 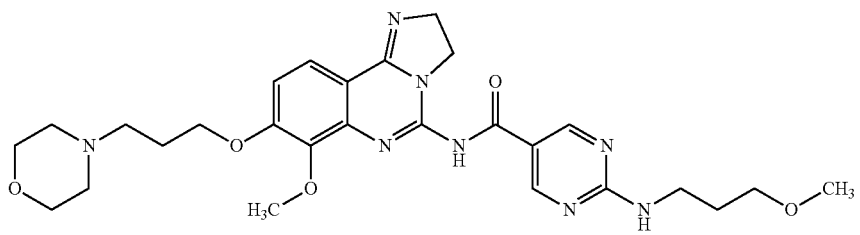 [SMILES: COCCCNc1ncc(C(=O)NC2=Nc3c(ccc(OCCCN4CCOCC4)c3OC)C3=NCCN23)cn1] |
| 42 | 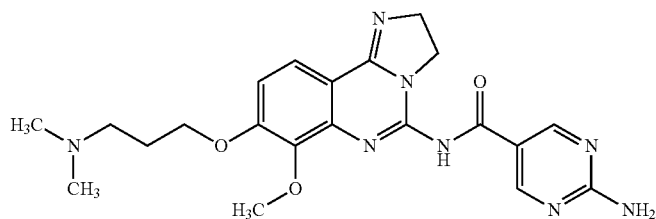 [SMILES: COc1c(OCCCN(C)C)ccc2c1N=C(NC(=O)c1cnc(N)nc1)N1CCN=C21] |
| 43 | 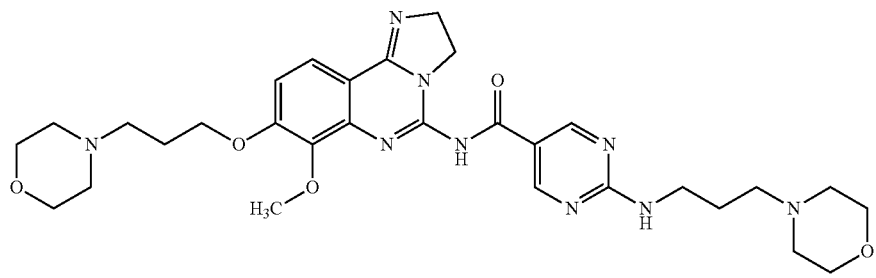 [SMILES: COc1c(OCCCN2CCOCC2)ccc2c1N=C(NC(=O)c1cnc(NCCCN3CCOCC3)nc1)N1CCN=C21] |
| 44 | 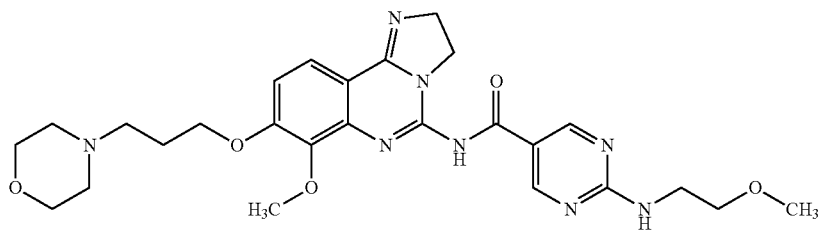 [SMILES: COCCNc1ncc(C(=O)NC2=Nc3c(ccc(OCCCN4CCOCC4)c3OC)C3=NCCN23)cn1] |
| 45 | 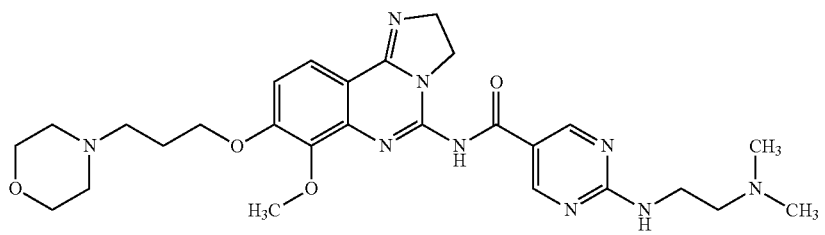 [SMILES: COc1c(OCCCN2CCOCC2)ccc2c1N=C(NC(=O)c1cnc(NCCN(C)C)nc1)N1CCN=C21] |

-continued
| Example | Structure |
|---|---|
| 46 | 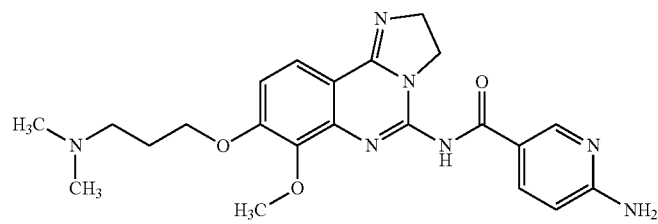 [SMILES: COc1c(OCCCN(C)C)ccc2c1N=C(NC(=O)c1ccc(N)nc1)N1CCN=C21] |
| 47 | 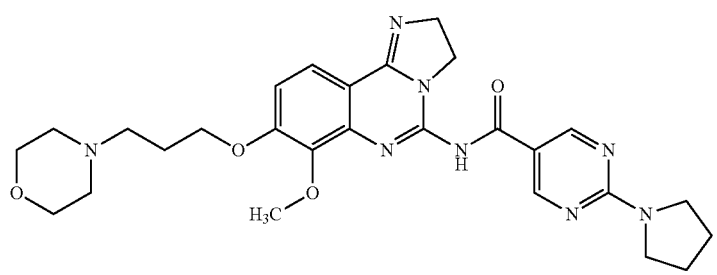 [SMILES: COc1c(OCCCN2CCOCC2)ccc2c1N=C(NC(=O)c1cnc(N3CCCC3)nc1)N1CCN=C21] |
| 48 | 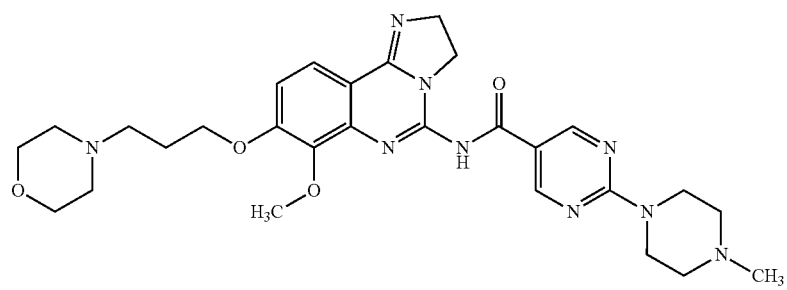 [SMILES: COc1c(OCCCN2CCOCC2)ccc2c1N=C(NC(=O)c1cnc(N3CCN(C)CC3)nc1)N1CCN=C21] |
| 49 | 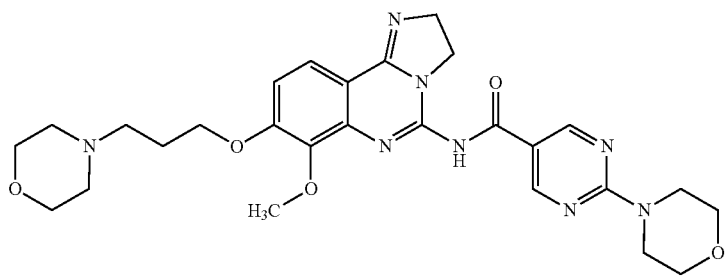 [SMILES: COc1c(OCCCN2CCOCC2)ccc2c1N=C(NC(=O)c1cnc(N3CCOCC3)nc1)N1CCN=C21] |
| 50 | 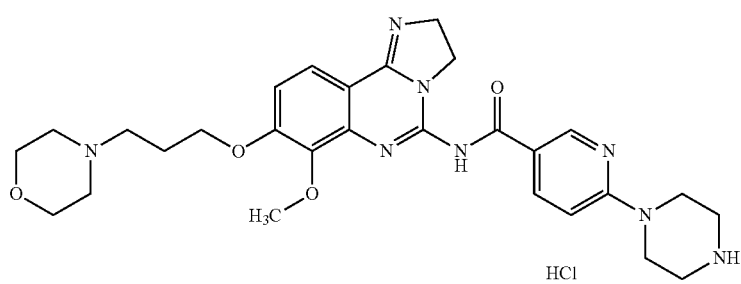 [SMILES: COc1c(OCCCN2CCOCC2)ccc2c1N=C(NC(=O)c1ccc(N3CCNCC3)nc1)N1CCN=C21 ; Cl] |

| Example | Structure |
|---|---|
| 51 | (structure: morpholine-propoxy, methoxy-substituted dihydroimidazo-quinazoline linked via amide to pyridine bearing (3S)-3-aminopyrrolidin-1-yl; HCl salt) |
| 52 | (structure: morpholine-propoxy, methoxy-substituted dihydroimidazo-quinazoline linked via amide to pyridine bearing (3R)-3-aminopyrrolidin-1-yl; HCl salt) |
| 53 | (structure: morpholine-propoxy, methoxy-substituted dihydroimidazo-quinazoline linked via amide to pyridine bearing 4-fluorobenzylamino group) |
| 54 | (structure: morpholine-propoxy, methoxy-substituted dihydroimidazo-quinazoline linked via amide to pyridine bearing furfurylamino group) |
| 55 | (structure: morpholine-propoxy, methoxy-substituted dihydroimidazo-quinazoline linked via amide to pyridine bearing 2-methoxyethylamino group) |

| Example | Structure |
|---|---|
| 56 | 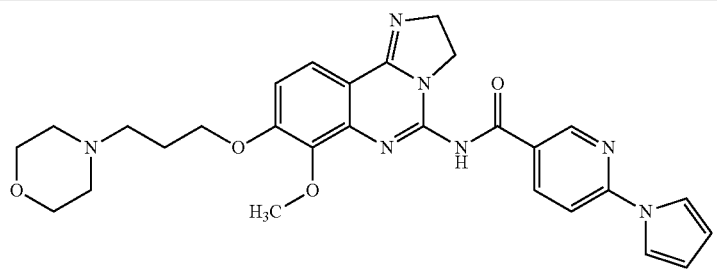 [SMILES: COc1c(OCCCN2CCOCC2)ccc2c1N=C(NC(=O)c1ccc(-n3cccc3)nc1)N1CCN=C21] |
| 57 | 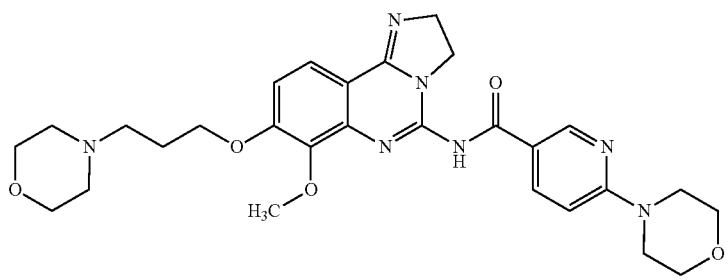 [SMILES: COc1c(OCCCN2CCOCC2)ccc2c1N=C(NC(=O)c1ccc(N3CCOCC3)nc1)N1CCN=C21] |
| 58 | 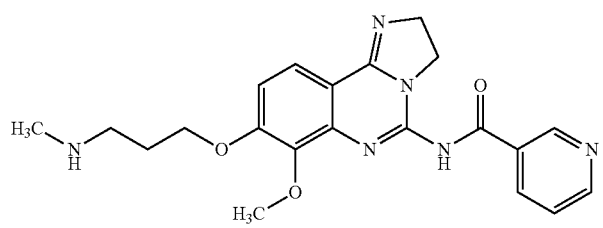 [SMILES: CNCCCOc1ccc2c(c1OC)N=C(NC(=O)c1cccnc1)N1CCN=C21] |
| 59 | 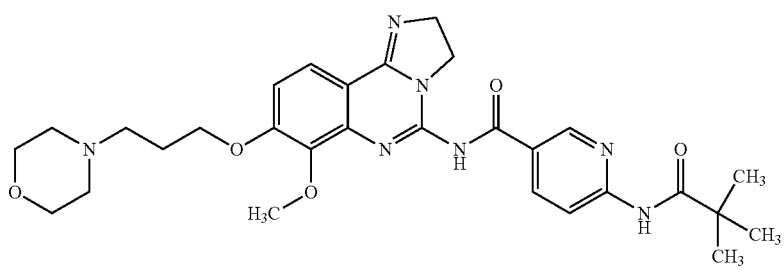 [SMILES: COc1c(OCCCN2CCOCC2)ccc2c1N=C(NC(=O)c1ccc(NC(=O)C(C)(C)C)nc1)N1CCN=C21] |
| 60 | 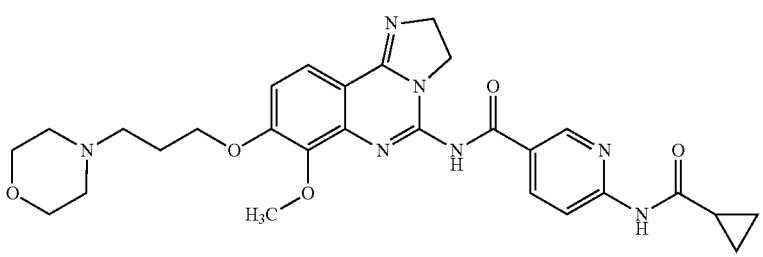 [SMILES: COc1c(OCCCN2CCOCC2)ccc2c1N=C(NC(=O)c1ccc(NC(=O)C3CC3)nc1)N1CCN=C21] |
| 61 | 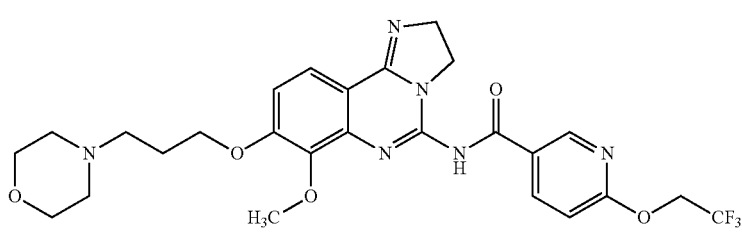 [SMILES: COc1c(OCCCN2CCOCC2)ccc2c1N=C(NC(=O)c1ccc(OCC(F)(F)F)nc1)N1CCN=C21] |

-continued
| Example | Structure |
|---|---|
| 62 | 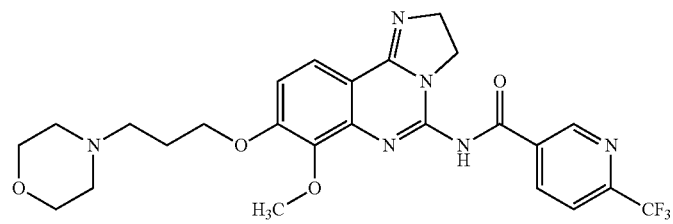 [SMILES: COc1c(OCCCN2CCOCC2)ccc2c1N=C(NC(=O)c1ccc(C(F)(F)F)nc1)N1CCN=C21] |
| 63 | 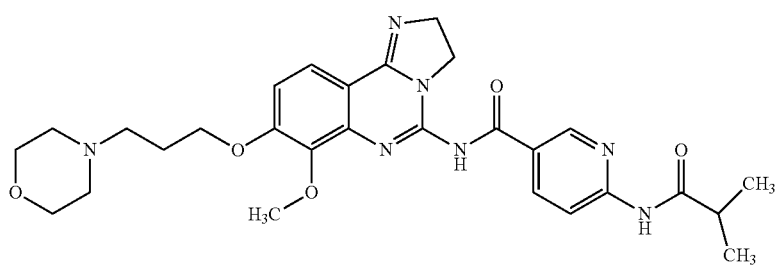 [SMILES: COc1c(OCCCN2CCOCC2)ccc2c1N=C(NC(=O)c1ccc(NC(=O)C(C)C)nc1)N1CCN=C21] |
| 64 | 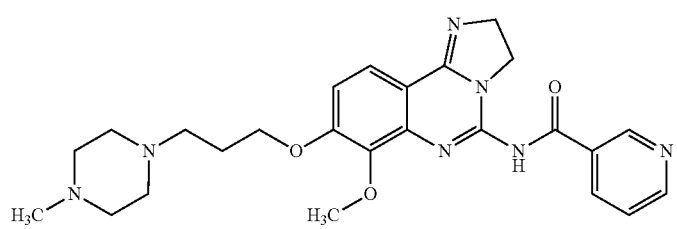 [SMILES: COc1c(OCCCN2CCN(C)CC2)ccc2c1N=C(NC(=O)c1cccnc1)N1CCN=C21] |
| 65 | 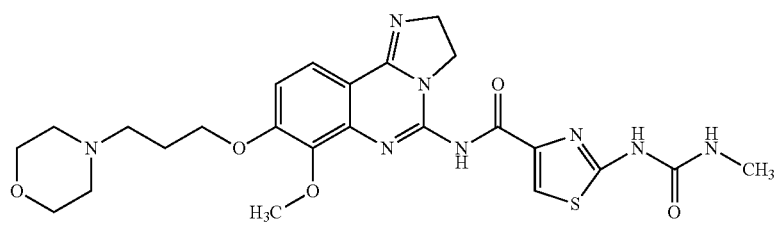 [SMILES: CNC(=O)Nc1nc(C(=O)NC2=Nc3c(ccc(OCCCN4CCOCC4)c3OC)C3=NCCN23)cs1] |
| 66 | 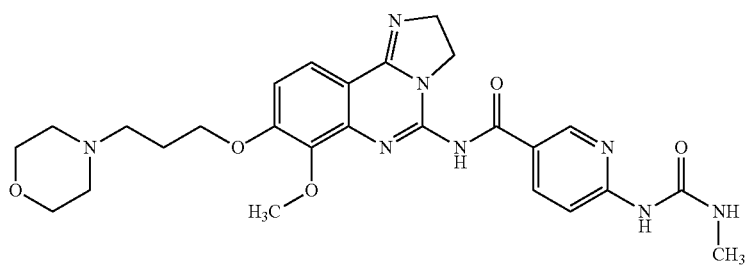 [SMILES: CNC(=O)Nc1ccc(C(=O)NC2=Nc3c(ccc(OCCCN4CCOCC4)c3OC)C3=NCCN23)cn1] |
| 67 | 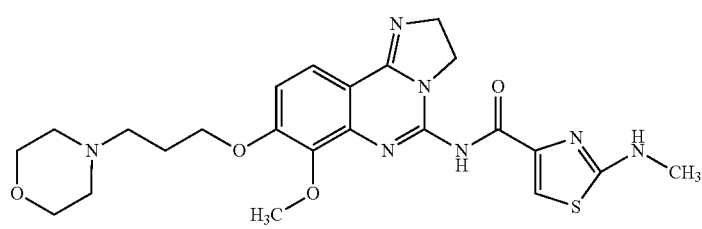 [SMILES: CNc1nc(C(=O)NC2=Nc3c(ccc(OCCCN4CCOCC4)c3OC)C3=NCCN23)cs1] |

| Example | Structure |
|---|---|
| 68 | 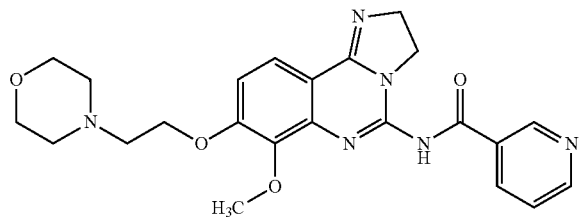 [SMILES: COc1c(OCCN2CCOCC2)ccc2c1N=C(NC(=O)c1cccnc1)N1CCN=C21] |
| 69 | 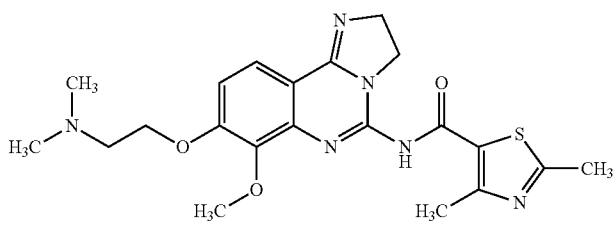 |
| 70 | 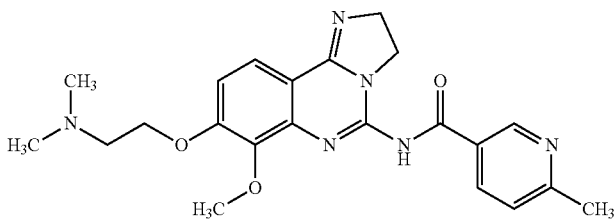 |
| 71 | 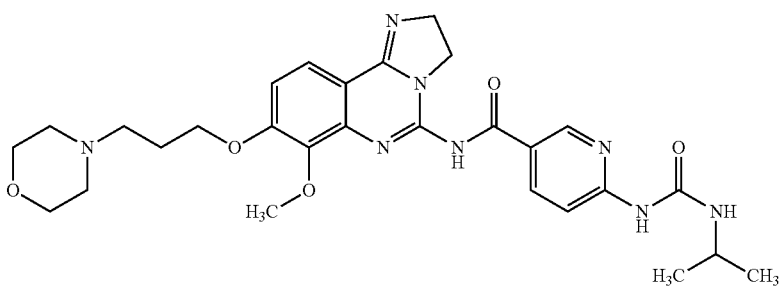 [SMILES: COc1c(OCCCN2CCOCC2)ccc2c1N=C(NC(=O)c1ccc(NC(=O)NC(C)C)nc1)N1CCN=C21] |
| 72 | 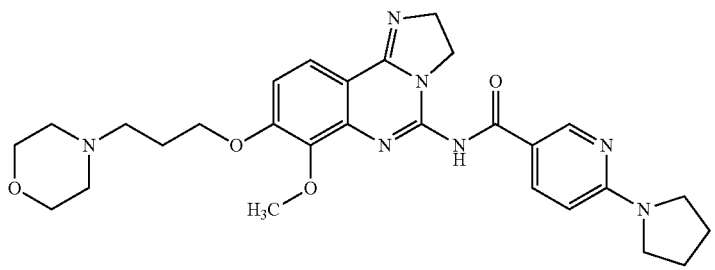 [SMILES: COc1c(OCCCN2CCOCC2)ccc2c1N=C(NC(=O)c1ccc(N3CCCC3)nc1)N1CCN=C21] |
| 73 | 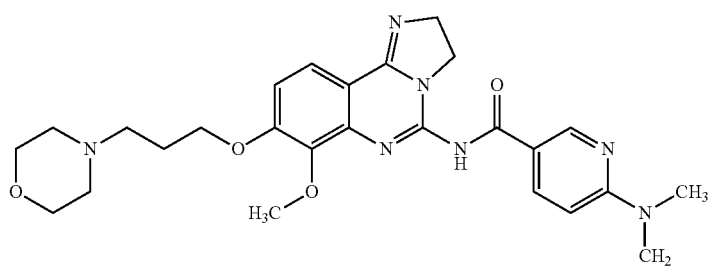 [SMILES: COc1c(OCCCN2CCOCC2)ccc2c1N=C(NC(=O)c1ccc(N(C)C)nc1)N1CCN=C21] |

| Example | Structure |
|---|---|
| 74 | 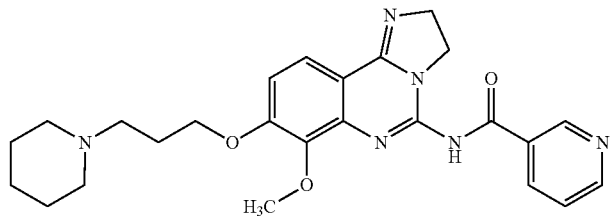 [SMILES: COc1c(OCCCN2CCCCC2)ccc2c1N=C(NC(=O)c1cccnc1)N1CCN=C21] |
| 75 | 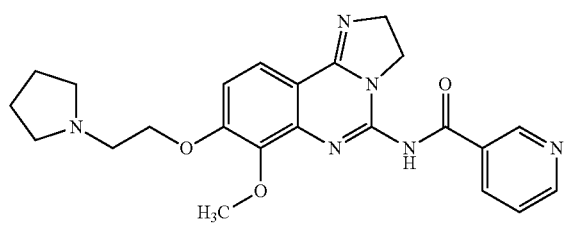 [SMILES: COc1c(OCCN2CCCC2)ccc2c1N=C(NC(=O)c1cccnc1)N1CCN=C21] |
| 76 | 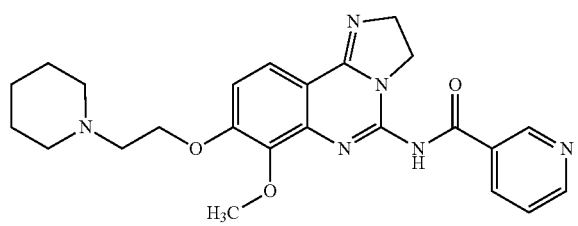 [SMILES: COc1c(OCCN2CCCCC2)ccc2c1N=C(NC(=O)c1cccnc1)N1CCN=C21] |
| 77 | 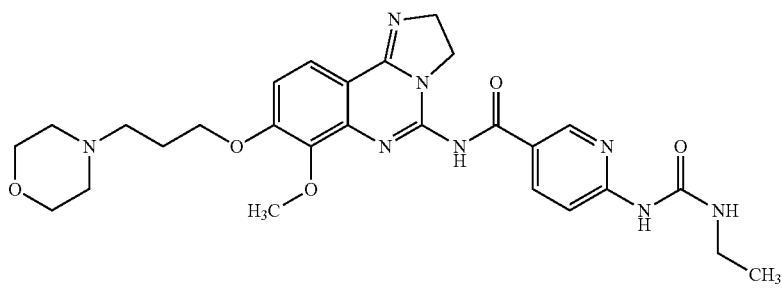 [SMILES: CCNC(=O)Nc1ccc(C(=O)NC2=Nc3c(ccc(OCCCN4CCOCC4)c3OC)C3=NCCN23)cn1] |
| 78 | 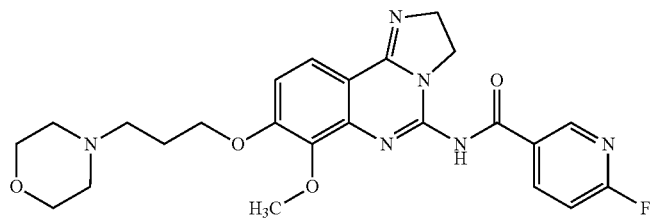 [SMILES: COc1c(OCCCN2CCOCC2)ccc2c1N=C(NC(=O)c1ccc(F)nc1)N1CCN=C21] |
| 79 | 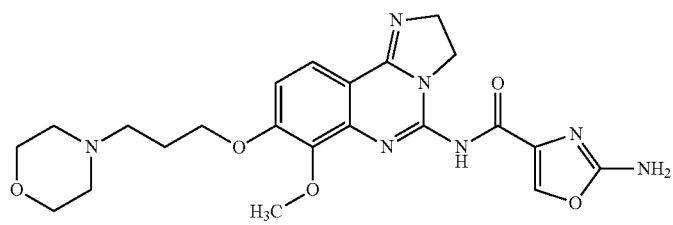 [SMILES: COc1c(OCCCN2CCOCC2)ccc2c1N=C(NC(=O)c1coc(N)n1)N1CCN=C21] |

-continued
| Example | Structure |
|---|---|
| 80 | 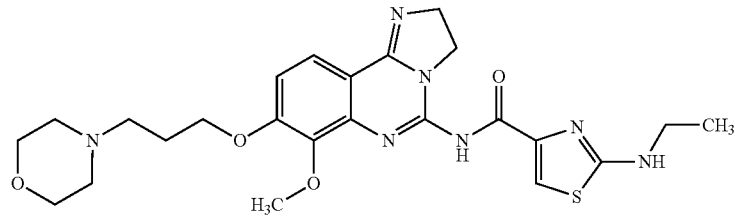 [SMILES: CCNc1nc(C(=O)NC2=Nc3c(ccc(OCCCN4CCOCC4)c3OC)C3=NCCN23)cs1] |
| 81 | 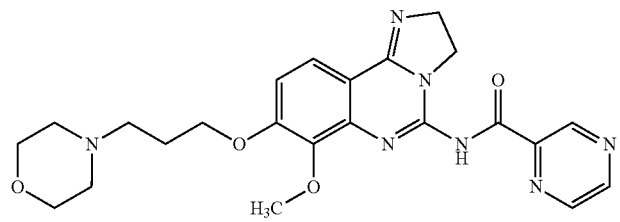 [SMILES: COc1c(OCCCN2CCOCC2)ccc2c1N=C(NC(=O)c1cnccn1)N1CCN=C21] |
| 82 | 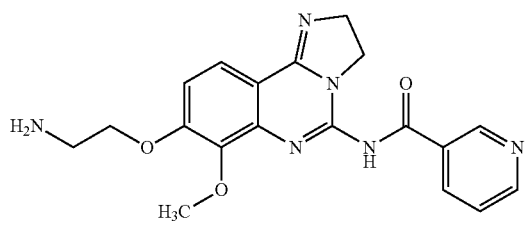 [SMILES: COc1c(OCCN)ccc2c1N=C(NC(=O)c1cccnc1)N1CCN=C21] |
| 83 | 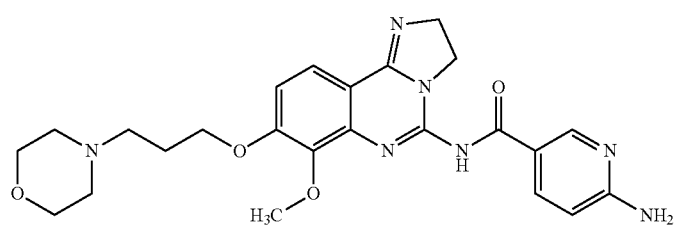 [SMILES: COc1c(OCCCN2CCOCC2)ccc2c1N=C(NC(=O)c1ccc(N)nc1)N1CCN=C21] |
| 84 | 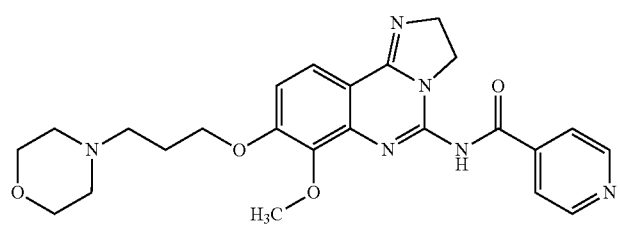 |
| 85 | 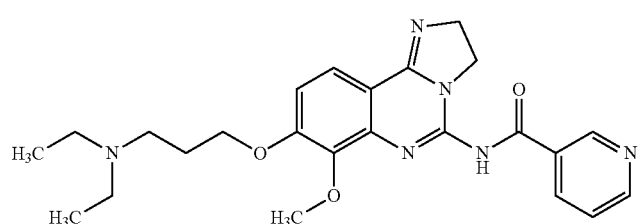 |
| 86 | 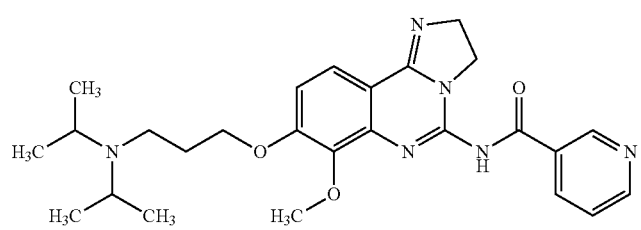 [SMILES: COc1c(OCCCN(C(C)C)C(C)C)ccc2c1N=C(NC(=O)c1cccnc1)N1CCN=C21] |

-continued

| Example | Structure |
|---|---|
| 87 | (chemical structure) |
| 88 | (chemical structure) |
| 89 | (chemical structure) |
| 90 | (chemical structure) |
| 91 | (chemical structure) |
| 92 | (chemical structure) |

| Example | Structure |
|---|---|
| 93 | 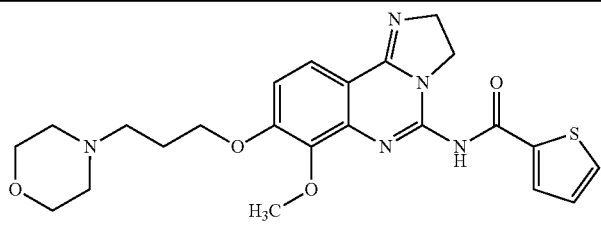 |
| 94 | 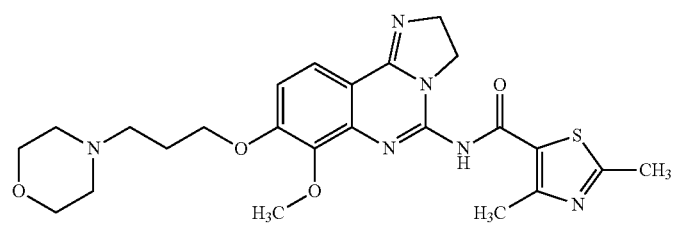 [SMILES: COc1c(OCCCN2CCOCC2)ccc2c1N=C(NC(=O)c1sc(C)nc1C)N1CCN=C21] |
| 95 | 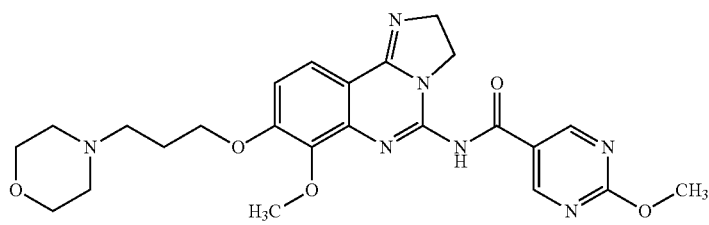 |
| 96 | 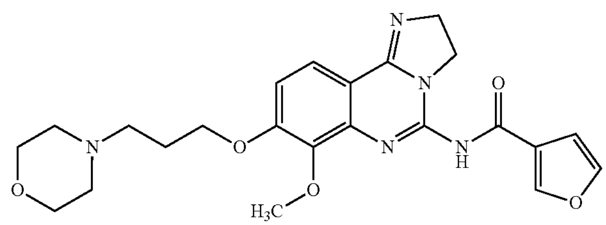 |
| 97 | 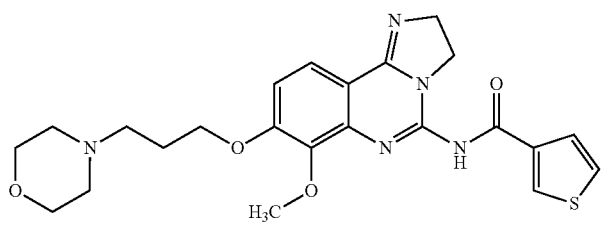 [SMILES: COc1c(OCCCN2CCOCC2)ccc2c1N=C(NC(=O)c1ccoc1)N1CCN=C21] |
| 98 | 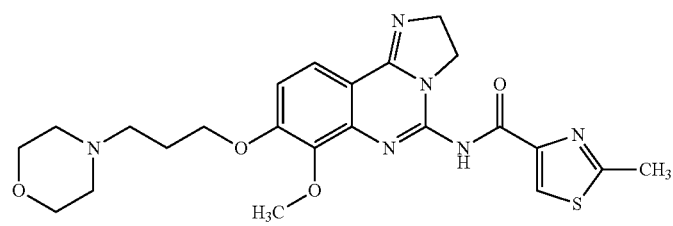 [SMILES: COc1c(OCCCN2CCOCC2)ccc2c1N=C(NC(=O)c1csc(C)n1)N1CCN=C21] |
| 99 | 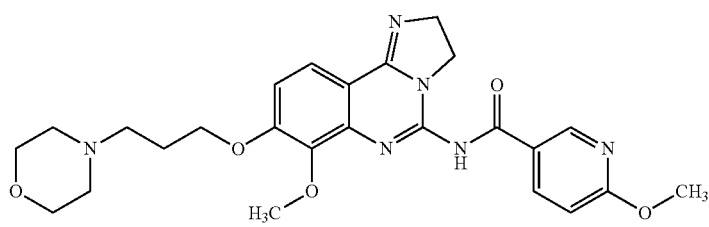 [SMILES: COc1ccc(C(=O)NC2=Nc3c(ccc(OCCCN4CCOCC4)c3OC)C3=NCCN23)cn1] |

| Example | Structure |
|---|---|
| 100 | 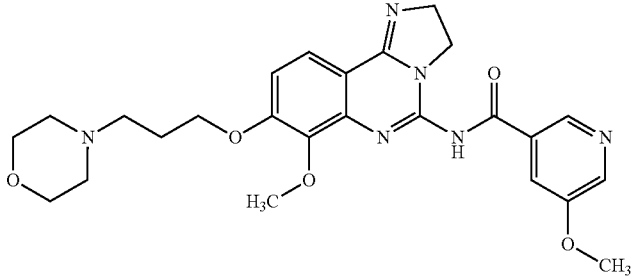 [SMILES: COc1cncc(C(=O)NC2=Nc3c(ccc(OCCCN4CCOCC4)c3OC)C3=NCCN23)c1] |
| 101 | 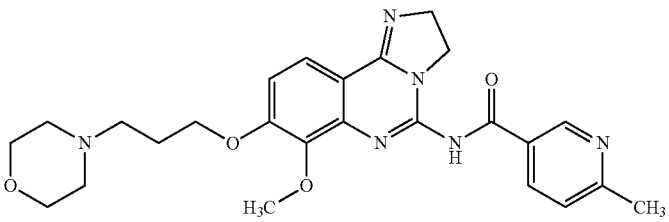 [SMILES: COc1c(OCCCN2CCOCC2)ccc2c1N=C(NC(=O)c1ccc(C)nc1)N1CCN=C21] |
| 102 | 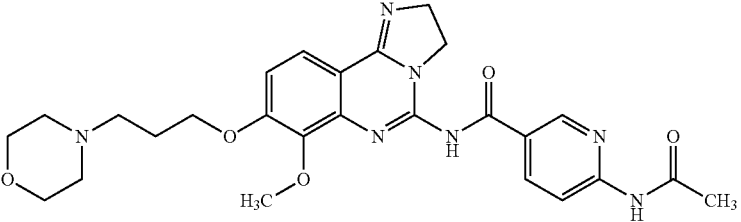 [SMILES: COc1c(OCCCN2CCOCC2)ccc2c1N=C(NC(=O)c1ccc(NC(C)=O)nc1)N1CCN=C21] |
| 103 | 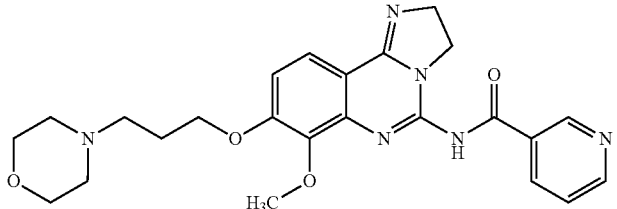 | or a physiologically acceptable salt, solvate, hydrate or stereoisomer thereof,

Said compounds are published as specific compound Examples 1 to 103 in International patent application PCT/US2007/024985, published as WO 2008/070150 A1 on Jun. 12, 2008, which is incorporated herein by reference in its entirety. In WO 2008/070150, said specific compound Examples may be synthesized according to the Examples. Biological test data for certain of said compounds are given therein on pp. 101 to 107.

Specifically, component A may be 2-amino-N-[7-methoxy-8-(3-morpholin-4-ylpropoxy)-2,3-dihydroimidazo[1,2-c]quinazolin-5-yl]pyrimidine-5-carboxamide dihydrochloride, (which is hereinafter referred to as "compound A" or "cpd. A") is published in international patent application PCT/EP2012/055600, published as WO 2012/136553 on Oct. 11, 2012, (which is incorporated herein by reference in its entirety), as the compound of Examples 1 and 2: 2-amino-N-[7-methoxy-8-(3-morpholin-4-ylpropoxy)-2,3-dihydroimidazo[1,2-c]quinazolin-5-yl]pyrimidine-5-carboxamide dihydrochloride: it may be synthesized according to the methods given in said Examples 1 and 2.

Said component A may be in the form of a pharmaceutical formulation which is ready for use to be administered simultaneously, concurrently, separately or sequentially. The components may be administered independnently of one another by the oral, intravenous, topical, local installations, intraperitoneal or nasal route.

In accordance with an embodiment of the above-mentioned aspects of the present invention, said combinations are of:

component B: anti-Programmed Cell Death Protein 1 (also referred to as "PD-1" or "CD279" (cluster of differentiation 279)) antibody (anti-PD-1 mAb).

Said component B may be in the form of a pharmaceutical formulation which is ready for use to be administered simultaneously, concurrently, separately or sequentially. The components may be administered independnently of one another by the oral, intravenous, topical, local installations, intraperitoneal or nasal route.

In accordance with an embodiment of the above-mentioned aspects of the present invention, said combinations are of:

component A: 2-amino-N-[7-methoxy-8-(3-morpholin-4-yl-propoxy)-2,3-dihydroimidazo[1,2-c]quinazolin-5-yl]pyrimidine-5-carboxamide or 2-amino-N-[7-methoxy-8-(3-morpholin-4-ylpropoxy)-2,3-dihydroimid-azo[1,2-c]

quinazolin-5-yl]pyrimidine-5-carboxamide dihydrochloride, (which is hereinafter referred to as "compound A" or "cpd. A")
and
component B: anti-Programmed Cell Death Protein 1 (also referred to as "PD-1" or "CD279" (cluster of differentiation 279)) antibody (anti-PD-1 mAb).

In accordance with an embodiment of the above-mentioned aspects of the present invention, said anti-Programmed Cell Death Protein 1 (also referred to as "PD-1" or "CD279" (cluster of differentiation 279)) antibody (anti-PD-1 mAb) is pembrolizumab, nivolumab, pidilizumab, or tislelizumab.

In accordance with an embodiment of the above-mentioned aspects of the present invention:
said component A is 2-amino-N-[7-methoxy-8-(3-morpholin-4-ylpropoxy)-2,3-dihydroimidazo[1,2-c]quinazolin-5-yl]pyrimidine-5-carboxamide, and:
said anti-Programmed Cell Death Protein 1 (also referred to as "PD-1" or "CD279" (cluster of differentiation 279)) antibody (anti-PD-1 mAb) is pembrolizumab.

In accordance with an embodiment of the above-mentioned aspects of the present invention:
said component A is 2-amino-N-[7-methoxy-8-(3-morpholin-4-ylpropoxy)-2,3-dihydroimidazo[1,2-c]quinazolin-5-yl]pyrimidine-5-carboxamide dihydrochloride, and:
said anti-Programmed Cell Death Protein 1 (also referred to as "PD-1" or "CD279" (cluster of differentiation 279)) antibody (anti-PD-1 mAb) is pembrolizumab.

In accordance with an embodiment of the above-mentioned aspects of the present invention, said anti-Programmed Cell Death Protein 1 (also referred to as "PD-1" or "CD279" (cluster of differentiation 279)) antibody (anti-PD-1 mAb) is nivolumab.

In accordance with an embodiment of the above-mentioned aspects of the present invention:
said component A is 2-amino-N-[7-methoxy-8-(3-morpholin-4-ylpropoxy)-2,3-dihydroimidazo[1,2-c]quinazolin-5-yl]pyrimidine-5-carboxamide, and:
said anti-Programmed Cell Death Protein 1 (also referred to as "PD-1" or "CD279" (cluster of differentiation 279)) antibody (anti-PD-1 mAb) is nivolumab.

In accordance with an embodiment of the above-mentioned aspects of the present invention:
said component A is 2-amino-N-[7-methoxy-8-(3-morpholin-4-ylpropoxy)-2,3-dihydroimidazo[1,2-c]quinazolin-5-yl]pyrimidine-5-carboxamide dihydrochloride, and:
said anti-Programmed Cell Death Protein 1 (also referred to as "PD-1" or "CD279" (cluster of differentiation 279)) antibody (anti-PD-1 mAb) is nivolumab.

Said component B may be in the form of a pharmaceutical formulation which is ready for use to be administered simultaneously, concurrently, separately or sequentially. The components may be administered independnently of one another by the oral, intravenous, topical, local installations, intraperitoneal or nasal route.

In accordance with an embodiment, the present invention relates to a combination of any component A mentioned herein with any component B mentioned herein.

In a particular embodiment, the present invention relates to a combination of a component A with a component B, as mentioned in the Examples section herein.

Useful Forms of Components A and B of the Combinations of the Present Invention

As mentioned supra, either or both of components A and B of any of the combinations of the present invention may be in a useful form, such as pharmaceutically acceptable salts, co-precipitates, metabolites, hydrates, solvates and prodrugs of all the compounds of examples. The term "pharmaceutically acceptable salt" refers to a relatively non-toxic, inorganic or organic acid addition salt of a compound of the present invention. For example, see S. M. Berge, et aL "Pharmaceutical Salts," *J. Pharm. Sci.* 1977, 66, 1-19. Pharmaceutically acceptable salts include those obtained by reacting the main compound, functioning as a base, with an inorganic or organic acid to form a salt, for example, salts of hydrochloric acid, sulfuric acid, phosphoric acid, methane sulfonic acid, camphor sulfonic acid, oxalic acid, maleic acid, succinic acid and citric acid. Pharmaceutically acceptable salts also include those in which the main compound functions as an acid and is reacted with an appropriate base to form, e.g., sodium, potassium, calcium, magnesium, ammonium, and chorine salts. Those skilled in the art will further recognize that acid addition salts of the claimed compounds may be prepared by reaction of the compounds with the appropriate inorganic or organic acid via any of a number of known methods. Alternatively, alkali and alkaline earth metal salts of acidic compounds of the invention are prepared by reacting the compounds of the invention with the appropriate base via a variety of known methods.

Representative salts of the compounds of this invention include the conventional non-toxic salts and the quaternary ammonium salts which are formed, for example, from inorganic or organic acids or bases by means well known in the art. For example, such acid addition salts include acetate, adipate, alginate, ascorbate, aspartate, benzoate, benzenesulfonate, bisulfate, butyrate, citrate, camphorate, camphorsulfonate, cinnamate, cyclopentanepropionate, digluconate, dodecylsulfate, ethanesulfonate, fumarate, glucoheptanoate, glycerophosphate, hemisulfate, heptanoate, hexanoate, chloride, bromide, iodide, 2-hydroxyethanesulfonate, itaconate, lactate, maleate, mandelate, methanesulfonate, 2-naphthalenesulfonate, nicotinate, nitrate, oxalate, pamoate, pectinate, persulfate, 3-phenylpropionate, picrate, pivalate, propionate, succinate, sulfonate, sulfate, tartrate, thiocyanate, tosylate, and undecanoate.

Base salts include alkali metal salts such as potassium and sodium salts, alkaline earth metal salts such as calcium and magnesium salts, and ammonium salts with organic bases such as dicyclohexylamine and N-methyl-D-glucamine. Additionally, basic nitrogen containing groups may be quaternized with such agents as lower alkyl halides such as methyl, ethyl, propyl, or butyl chlorides, bromides and iodides; dialkyl sulfates like dimethyl, diethyl, dibutyl sulfate, or diamyl sulfates, long chain halides such as decyl, lauryl, myristyl and strearyl chlorides, bromides and iodides, aralkyl halides like benzyl and phenethyl bromides and others.

A solvate for the purpose of this invention is a complex of a solvent and a compound of the invention in the solid state. Exemplary solvates would include, but are not limited to, complexes of a compound of the invention with ethanol or methanol. Hydrates are a specific form of solvate wherein the solvent is water.

Pharmaceutical Formulations of Components A and B of the Combinations of the Present Invention As mentioned supra, the components A or B may, independently from one another, be in the form of a pharmaceutical composition or formulation which is ready for use to be administered simultaneously, concurrently, separately or sequentially. The components may be administered independently of one another by the oral, intravenous, topical, local installations, intraperitoneal or nasal route.

Said compositions can be utilized to achieve the desired pharmacological effect by administration to a patient in need thereof. A patient, for the purpose of this invention, is a mammal, including a human, in need of treatment for the particular condition or disease. Therefore, the present invention includes combinations in which components A and B, independently of one another, are pharmaceutical formulations compositions that are comprised of a pharmaceutically acceptable carrier and a pharmaceutically effective amount of a said component. A pharmaceutically acceptable carrier is preferably a carrier that is relatively non-toxic and innocuous to a patient at concentrations consistent with effective activity of the active ingredient so that any side effects ascribable to the carrier do not vitiate the beneficial effects of component, and/or combination. A pharmaceutically effective amount of a combination is preferably that amount which produces a result or exerts an influence on the particular condition being treated. The combinations of the present invention can be administered with pharmaceutically-acceptable carriers well known in the art using any effective conventional dosage unit forms, including immediate, slow and timed release preparations, orally, parenterally, topically, nasally, ophthalmically, optically, sublingually, rectally, vaginally, and the like.

It is possible for the compounds according to the invention to have systemic and/or local activity. For this purpose, they can be administered in a suitable manner, such as, for example, via the oral, parenteral, pulmonary, nasal, sublingual, lingual, buccal, rectal, vaginal, dermal, transdermal, conjunctival, otic route or as an implant or stent.

For these administration routes, it is possible for the compounds according to the invention to be administered in suitable administration forms.

For oral administration, it is possible to formulate the compounds according to the invention to dosage forms known in the art that deliver the compounds of the invention rapidly and/or in a modified manner, such as, for example, tablets (uncoated or coated tablets, for example with enteric or controlled release coatings that dissolve with a delay or are insoluble), orally-disintegrating tablets, films/wafers, films/lyophylisates, capsules (for example hard or soft gelatine capsules), sugar-coated tablets, granules, pellets, powders, emulsions, suspensions, aerosols or solutions. It is possible to incorporate the compounds according to the invention in crystalline and/or amorphised and/or dissolved form into said dosage forms.

Parenteral administration can be effected with avoidance of an absorption step (for example intravenous, intraarterial, intracardial, intraspinal or intralumbal) or with inclusion of absorption (for example intramuscular, subcutaneous, intracutaneous, percutaneous or intraperitoneal). Administration forms which are suitable for parenteral administration are, inter alia, preparations for injection and infusion in the form of solutions, suspensions, emulsions, lyophylisates or sterile powders.

Examples which are suitable for other administration routes are pharmaceutical forms for inhalation [inter alia powder inhalers, nebulizers], nasal drops, nasal solutions, nasal sprays; tablets/films/wafers/capsules for lingual, sublingual or buccal administration; suppositories; eye drops, eye ointments, eye baths, ocular inserts, ear drops, ear sprays, ear powders, ear-rinses, ear tampons; vaginal capsules, aqueous suspensions (lotions, mixturae agitandae), lipophilic suspensions, emulsions, ointments, creams, transdermal therapeutic systems (such as, for example, patches), milk, pastes, foams, dusting powders, implants or stents.

The compounds according to the invention can be incorporated into the stated administration forms. This can be effected in a manner known per se by mixing with pharmaceutically suitable excipients. Pharmaceutically suitable excipients include, inter alia, fillers and carriers (for example cellulose, microcrystalline cellulose (such as, for example, Avicel®), lactose, mannitol, starch, calcium phosphate (such as, for example, Di-Cafos®)), ointment bases (for example petroleum jelly, paraffins, triglycerides, waxes, wool wax, wool wax alcohols, lanolin, hydrophilic ointment, polyethylene glycols), bases for suppositories (for example polyethylene glycols, cacao butter, hard fat), solvents (for example water, ethanol, isopropanol, glycerol, propylene glycol, medium chain-length triglycerides fatty oils, liquid polyethylene glycols, paraffins), surfactants, emulsifiers, dispersants or wetters (for example sodium dodecyl sulfate), lecithin, phospholipids, fatty alcohols (such as, for example, Lanette®), sorbitan fatty acid esters (such as, for example, Span®), polyoxyethylene sorbitan fatty acid esters (such as, for example, Tween®), polyoxyethylene fatty acid glycerides (such as, for example, Cremophor®), polyoxethylene fatty acid esters, polyoxyethylene fatty alcohol ethers, glycerol fatty acid esters, poloxamers (such as, for example, Pluronic®), buffers, acids and bases (for example phosphates, carbonates, citric acid, acetic acid, hydrochloric acid, sodium hydroxide solution, ammonium carbonate, trometamol, triethanolamine), isotonicity agents (for example glucose, sodium chloride), adsorbents (for example highly-disperse silicas), viscosity-increasing agents, gel formers, thickeners and/or binders (for example polyvinylpyrrolidone, methylcellulose, hydroxypropylmethylcellulose, hydroxypropyl-cellulose, carboxymethylcellulose-sodium, starch, carbomers, polyacrylic acids (such as, for example, Carbopor); alginates, gelatine), disintegrants (for example modified starch, carboxymethylcellulose-sodium, sodium starch glycolate (such as, for example, Explotab®), cross- linked polyvinylpyrrolidone, croscarmellose-sodium (such as, for example, AcDiSol®)), flow regulators, lubricants, glidants and mould release agents (for example magnesium stearate, stearic acid, talc, highly-disperse silicas (such as, for example, Aerosil®)), coating materials (for example sugar, shellac) and film formers for films or diffusion membranes which dissolve rapidly or in a modified manner (for example polyvinylpyrrolidones (such as, for example, Kollidon®), polyvinyl alcohol, hydroxypropylmethylcellulose, hydroxypropylcellulose, ethylcellulose, hydroxypropyl-methylcellulose phthalate, cellulose acetate, cellulose acetate phthalate, polyacrylates, polymethacrylates such as, for example, Eudragit®)), capsule materials (for example gelatine, hydroxypropylmethylcellulose), synthetic polymers (for example polylactides, polyglycolides, polyacrylates, polymethacrylates (such as, for example, Eudragit®), polyvinylpyrrolidones (such as, for example, Kollidon®), polyvinyl alcohols, polyvinyl acetates, polyethylene oxides, polyethylene glycols and their copolymers and blockcopolymers), plasticizers (for example polyethylene glycols, propylene glycol, glycerol, triacetine, triacetyl citrate, dibutyl phthalate), penetration enhancers, stabilisers (for example antioxidants such as, for example, ascorbic acid, ascorbyl palmitate, sodium ascorbate, butylhydroxyanisole, butylhydroxytoluene, propyl gallate), preservatives (for example parabens, sorbic acid, thiomersal, benzalkonium chloride, chlorhexidine acetate, sodium benzoate), colourants (for example inorganic pigments such as, for example, iron oxides, titanium dioxide), flavourings, sweeteners, flavour- and/or odour-masking agents.

The present invention furthermore relates to a pharmaceutical composition which comprise at least one compound according to the invention, conventionally together with one or more pharmaceutically suitable excipient(s), and to their use according to the present invention.

Method of Treating Cancer

Within the context of the present invention, the term "cancer" includes, but is not limited to, cancers of the breast, lung, brain, reproductive organs, digestive tract, urinary tract, liver, eye, skin, head and neck, thyroid, parathyroid and their distant metastases. Those disorders also include multiple myeloma, lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, medulloblastoma, ependymoma, as well as neuroectodermal and pineal tumor.

Tumors of the male reproductive organs include, but are not limited to prostate and testicular cancer. Tumors of the female reproductive organs include, but are not limited to endometrial, cervical, ovarian, vaginal, and vulvar cancer, as well as sarcoma of the uterus.

Tumors of the digestive tract include, but are not limited to anal, colon, colorectal, esophageal, gallbladder, gastric, pancreatic, rectal, small-intestine, and salivary gland cancers.

Tumors of the urinary tract include, but are not limited to bladder, penile, kidney, renal pelvis, ureter, urethral and human papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer and squamous cell.

Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

The present invention relates to a method for using the combinations of the present invention, in the treatment or prophylaxis of a cancer, particularly (but not limited to) colorectal cancer, lung cancer, breast cancer, prostate cancer, bladder cancer, gastric cancer, head and neck cancer, liver cancer, brain cancer, melanoma, ovarian cancer, pancreatic cancer, kidney cancer, endometrial cancer, lymphoma, leukemia, etc. Combinations can be utilized to inhibit, block, reduce, decrease, etc., cell proliferation and/or cell division, and/or produce apoptosis, in the treatment or prophylaxis of cancer, in particular (but not limited to) colorectal cancer, lung cancer, breast cancer, prostate cancer, bladder cancer, gastric cancer, head and neck cancer, liver cancer, brain cancer, melanoma, ovarian cancer, pancreatic cancer, kidney cancer, endometrial cancer, lymphoma, leukemia, etc. This method comprises administering to a mammal in need thereof, including a human, an amount of a combination of this invention, or a pharmaceutically acceptable salt, isomer, polymorph, metabolite, hydrate, solvate or ester thereof; etc. which is effective for the treatment or prophylaxis of cancer, in particular (but not limited to) colorectal cancer, lung cancer, breast cancer, prostate cancer, bladder cancer, gastric cancer, head and neck cancer, liver cancer, brain cancer, melanoma, ovarian cancer, pancreatic cancer, kidney cancer, endometrial cancer, lymphoma, leukemia, etc.

The term "treating" or "treatment" as stated throughout this document is used conventionally, e.g., the management or care of a subject for the purpose of combating, alleviating, reducing, relieving, improving the condition of, etc., of a disease or disorder, such as a carcinoma.

Dose and Administration

Based upon standard laboratory techniques known to evaluate compounds useful for the treatment or prophylaxis of cancer, in particular (but not limited to) colorectal cancer, lung cancer, breast cancer, prostate cancer, bladder cancer, gastric cancer, head and neck cancer, liver cancer, brain cancer, melanoma, ovarian cancer, pancreatic cancer, kidney cancer, endometrial cancer, lymphoma, leukemia, etc., by standard toxicity tests and by standard pharmacological assays for the determination of treatment of the conditions identified above in mammals, and by comparison of these results with the results of known medicaments that are used to treat these conditions, the effective dosage of the combinations of this invention can readily be determined for treatment of the indication. The amount of the active ingredient to be administered in the treatment of the condition can vary widely according to such considerations as the particular combination and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, "drug holidays" in which a patient is not dosed with a drug for a certain period of time, may be beneficial to the overall balance between pharmacological effect and tolerability. A unit dosage may contain from about 0.5 mg to about 1,500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific combination employed, the age and general condition of the patient, time of administration, route of administration, rate of excretion of the drug, drug combinations, and the like. The desired mode of treatment and number of doses of a combination of the present invention or a pharmaceutically acceptable salt or ester or composition thereof can be ascertained by those skilled in the art using conventional treatment tests.

Therapies Using Combinations of Component A as Described Supra, Component B as Described Supra, and Component C: One or More Further Pharmaceutical Agents The combinations of component A and component B of this invention can be administered as the sole pharmaceutical agent or in combination with one or more further pharmaceutical agents where the resulting combination of components A, B and C causes no unacceptable adverse effects. For example, the combinations of components A and B of this invention can be combined with component C, i.e. one or more further pharmaceutical agents, such as known anti-angiogenesis, anti-hyper-proliferative, antiinflammatory, analgesic, immunoregulatory, diuretic, antiarrhytmic, anti-hypercholsterolemia, anti-dyslipidemia, anti-diabetic or antiviral agents, and the like, as well as with admixtures and combinations thereof.

Component C, can be one or more pharmaceutical agents such as 131I-chTNT, abarelix, abiraterone, aclarubicin, adalimumab, ado-trastuzumab emtansine, afatinib, aflibercept, aldesleukin, alectinib, alemtuzumab, alendronic acid, alitretinoin, altretamine, amifostine, aminoglutethimide, hexyl aminolevulinate, amrubicin, amsacrine, anastrozole, ancestim, anethole dithiolethione, anetumab ravtansine, angiotensin II, antithrombin III, aprepitant, arcitumomab, arglabin, arsenic trioxide, asparaginase, atezolizumab, axitinib, azacitidine, basiliximab, belotecan, bendamustine, besilesomab, belinostat, bevacizumab, bexarotene, bicalutamide, bisantrene, bleomycin, blinatumomab, bortezomib, buserelin, bosutinib, brentuximab vedotin, busulfan, cabazitaxel, cabozantinib, calcitonine, calcium folinate, calcium levofolinate, capecitabine, capromab, carbamazepine carboplatin, carboquone, carfilzomib, carmofur, carmustine, catumaxomab, celecoxib, celmoleukin, ceritinib, cetuximab, chlorambucil, chlormadinone, chlormethine, cidofovir, cinacalcet, cisplatin, cladribine, clodronic acid, clofarabine, cobimetinib, copanlisib, crisantaspase, crizotinib, cyclophosphamide, cyproterone, cytarabine, dacarbazine, dactinomycin, daratumumab, darbepoetin alfa, dabrafenib, dasatinib, daunorubicin, decitabine, degarelix, denileukin diftitox, denosumab, depreotide, deslorelin, dianhydrogalactitol, dexrazoxane, dibrospidium chloride, dianhydrogalactitol, diclofenac, dinutuximab, docetaxel, dolasetron, doxifluridine, doxorubicin, doxorubicin+estrone, dronabinol, eculizumab, edrecolomab, elliptinium acetate, elotuzumab, eltrombopag, endostatin, enocitabine, enzalutamide, epirubicin, epitiostanol, epoetin alfa, epoetin beta, epoetin zeta, eptaplatin, eribulin, erlotinib, esomeprazole, estradiol, estramustine, ethinylestradiol, etoposide, everolimus, exemestane, fadrozole, fentanyl, filgrastim, fluoxymesterone, floxuridine, fludarabine, fluorouracil, flutamide, folinic acid, formestane, fosaprepitant, fotemustine, fulvestrant, gadobutrol, gadoteridol, gadoteric acid meglumine, gadoversetamide, gadoxetic acid, gallium nitrate, ganirelix, gefitinib, gemcitabine, gemtuzumab, Glucarpidase, glutoxim, GM-CSF, goserelin, granisetron, granulocyte colony stimulating factor, histamine dihydrochloride, histrelin, hydroxycarbamide, I-125 seeds, lansoprazole, ibandronic acid, ibritumomab tiuxetan, ibrutinib, idarubicin, ifosfamide, imatinib, imiquimod, improsulfan, indisetron, incadronic acid, ingenol mebutate, interferon alfa, interferon beta, interferon gamma, iobitridol, iobenguane (123I), iomeprol, ipilimumab, irinotecan, Itraconazole, ixabepilone, ixazomib, lanreotide, lansoprazole, lapatinib, lasocholine, lenalidomide, lenvatinib, lenograstim, lentinan, letrozole, leuprorelin, levamisole, levonorgestrel, levothyroxine sodium, lisuride, lobaplatin, lomustine, lonidamine, masoprocol, medroxyprogesterone, megestrol, melarsoprol, melphalan, mepitiostane, mercaptopurine, mesna, methadone, methotrexate, methoxsalen, methylaminolevulinate, methylprednisolone, methyltestosterone, metirosine, mifamurtide, miltefosine, miriplatin, mitobronitol, mitoguazone, mitolactol, mitomycin, mitotane, mitoxantrone, mogamulizumab, molgramostim, mopidamol, morphine hydrochloride, morphine sulfate, nabilone, nabiximols, nafarelin, naloxone+pentazocine, naltrexone, nartograstim, necitumumab, nedaplatin, nelarabine, neridronic acid, netupitant/palonosetron, nivolumab, pentetreotide, nilotinib, nilutamide, nimorazole, nimotuzumab, nimustine, nintedanib, nitracrine, nivolumab, obinutuzumab, octreotide, ofatumumab, olaparib, olaratumab, omacetaxine mepesuccinate, omeprazole, ondansetron, oprelvekin, orgotein, orilotimod, osimertinib, oxaliplatin, oxycodone, oxymetholone, ozogamicine, p53 gene therapy, paclitaxel, palbociclib, palifermin, palladium-103 seed, palonosetron, pamidronic acid, panitumumab, panobinostat, pantoprazole, pazopanib, pegaspargase, PEG-epoetin beta (methoxy PEG-epoetin beta), pembrolizumab, pegfilgrastim, peginterferon alfa-2b, pembrolizumab, pemetrexed, pentazocine, pentostatin, peplomycin, Perflubutane, perfosfamide, Pertuzumab, picibanil, pilocarpine, pirarubicin, pixantrone, plerixafor, plicamycin, poliglusam, polyestradiol phosphate, polyvinylpyrrolidone+sodium hyaluronate, polysaccharide-K, pomalidomide, ponatinib, porfimer sodium, pralatrexate, prednimustine, prednisone, procarbazine, procodazole, propranolol, quinagolide, rabeprazole, racotumomab, radium-223 chloride, radotinib, raloxifene, raltitrexed, ramosetron, ramucirumab, ranimustine, rasburicase, razoxane, refametinib, regorafenib, risedronic acid, rhenium-186 etidronate, rituximab, rolapitant, romidepsin, romiplostim, romurtide, roniciclib, rucaparib, samarium (153Sm) lexidronam, sargramostim, satumomab, secretin, siltuximab, sipuleucel-T, sizofiran, sobuzoxane, sodium glycididazole, sonidegib, sorafenib, stanozolol, streptozocin, sunitinib, talaporfin, talimogene laherparepvec, tamibarotene, tamoxifen, tapentadol, tasonermin, teceleukin, technetium (99mTc) nofetumomab merpentan, 99mTc-HYNIC-[Tyr3]-octreotide, tegafur, tegafur+gimeracil+oteracil, temoporfin, temozolomide, temsirolimus, teniposide, testosterone, tetrofosmin, thalidomide, thiotepa, thymalfasin, thyrotropin alfa, tioguanine, tocilizumab, topotecan, toremifene, tositumomab, trabectedin, trametinib, tramadol, trastuzumab, trastuzumab emtansine, treosulfan, tretinoin, trifluridine+tipiracil, trilostane, triptorelin, trametinib, trofosfamide, thrombopoietin, tryptophan, ubenimex, valatinib, valrubicin, vandetanib, vapreotide, vemurafenib, vinblastine, vincristine, vindesine, vinflunine, vinorelbine, vismodegib, vorinostat, vorozole, yttrium-90 glass microspheres, zinostatin, zinostatin stimalamer, zoledronic acid, zorubicin.

Generally, the use of component C in combination with a combination of components A and B of the present invention will serve to:

(1) yield better efficacy in reducing the growth of a tumor or even eliminate the tumor as compared to administration of either agent alone,
(2) provide for the administration of lesser amounts of the administered chemotherapeutic agents,
(3) provide for a chemotherapeutic treatment that is well tolerated in the patient with fewer deleterious pharmacological complications than observed with single agent chemotherapies and certain other combined therapies,
(4) provide for treating a broader spectrum of different cancer types in mammals, especially humans,
(5) provide for a higher response rate among treated patients,
(6) provide for a longer survival time among treated patients compared to standard chemotherapy treatments,
(7) provide a longer time for tumor progression, and/or
(8) yield efficacy and tolerability results at least as good as those of the agents used alone, compared to known instances where other cancer agent combinations produce antagonistic effects.

The following Examples describe the feasability of the present invention, but not restricting the invention to these Examples only.

EXAMPLES

The following abbreviations are used in the Examples:

"Compound A" (or "cpd. A") means 2-amino-N-[7-methoxy-8-(3-morpholin-4-ylpropoxy) -2,3-dihydroimidazo[1,2-c]quinazolin-5-yl]pyrimidine-5-carboxamide dihydrochloride: it is published in international patent application PCT/EP2012/055600, published as WO 2012/136553 on Oct. 11, 2012, (which is incorporated herein by reference in its entirety), as the compound of Examples 1 and 2: 2-amino-N-[7-methoxy-8-(3-morpholin-4-yl-propoxy)-2,3-dihydroimidazo[1,2-c]quinazolin-5-yl]pyrimidine-5-carboxamide dihydrochloride: it may be synthesized according to the methods given in said Examples 1 and 2.

2-amino-N-[7-methoxy-8-(3-morpholin-4-ylpropoxy)-2,3-dihydroimidazo[1,2-c]quinazolin-5-yl]pyrimidine-5-carboxamide dihydrochloride is a compound of structure:

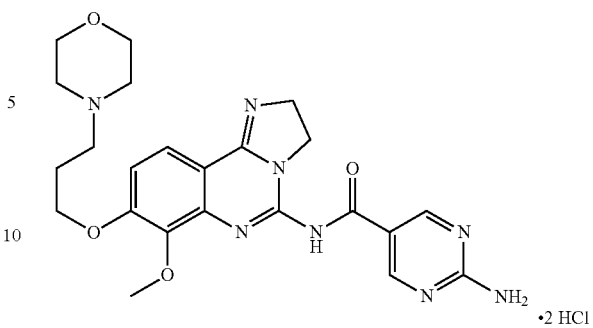

and is an example of component A as described and defined herein.

"Compound B" (or "cpd. B") means anti-Programmed Cell Death Protein 1 (also referred to as "PD-1" or "CD279" (cluster of differentiation 279)) antibody blocking the interaction of PD-1 (said antibody being also referred to as "anti-PD-1 mAb") and its ligand (said ligand being also referred to as "PD-L1" or "PD-L2") or "anti-mouse PD-1"), which is an example of component B as described and defined herein. The anti-mouse PD-1 (CD279) was purchased from Bio X Cell, 10 Technology Dr., Suite 2B, West Lebanon, N.H. 03784-1671, U.S.A., as clone RMP1-14, Catalog #: BE0146. This mouse anti-PD-1 showed similar effects on blocking the interaction of PD-1 and PD-L1/L2, as well as functional consequence on immune system as what have been observed with antibodies or inhibitors blocking human PD-1 and its ligand PD-L1/L2 interaction, such as (but not limited to), nivolumab (Opdivo), Pembrolizumab (Keytruda, Merck) (DrugBank Accession Number=DB09037), Pidilizumab (CT-011) Medivation), Tislelizumab (BGB-A317, BeiGene and Celgene), MEDI4736, MPDL3280A, etc.

In re. pembrolizumab (Keytruda, Merck) (DrugBank Accession Number=DB09037):

U.S. Pat. No. 8,354,509 (referred to as "'509"); U.S. Pat. No. 8,900,587 (referred to as "'587"). The '509 and '587 patents cover pembrolizumab as a composition of matter.

EP 2,170,959 (referred to also as "'959"). EP 2,170,959—UK, Germany, Spain, France, Italy. Keytruda (pembrolizumab) is indicated as monotherapy for the treatment of (1) advanced unresectable or metastatic melanoma and (2) locally advanced or metastatic non-small cell lung cancer in certain adults, and (3) relapsed or refractory classical Hodgkin lymphoma in certain adults. In July 2017, EMA's Committee for Medicinal Products for Human Use recommended approval for Keytruda for the treatment of certain patients with locally advanced or metastatic urothelial cancer. The '959 patent covers pembrolizumab as a composition of matter.

In re. Nivolumab (Opdivo, Bristol-Myers Squibb) (DrugBank Accession Number=DB09035 (DB06132):

U.S. Pat. No. 8,008,449 (referred to as "'449". The '449 patent is the composition-of-matter patent for nivolumab.

Experimental Methods

A20 diffuse large B cell lymphoma and CT26 colorectal cancer cells were maintained in vitro in cell cultural medium supplemented with serum (according to the instructions for each corresponding cell lines) at 37° C. in an atmosphere of 5% CO2 in air. The tumor cells were routinely subcultured twice weekly. The cells in an exponential growth phase were harvested and counted for tumor inoculation. To investigate anti-tumor efficacy and mechanisms of action in vivo, each mouse was inoculated subcutaneously at the right lower flank region with tumor cells ($1\times10^5$–$2\times10^6$ depending on the cell lines) in 0.1 ml of PBS with or without metrigel for tumor development. Before commencement of treatment, all animals were weighed and the tumor volumes were measured using a caliper. Since the tumor volume can affect the effectiveness of any given treatment, tumor volume was used as numeric parameter to randomize selected animals into specified groups to minimize the systematic error. The randomization was performed using matched distribution method. The treatments were started when the mean tumor size reached a predefined volume. The test article administration and the animal numbers in each study group were shown in the experimental design Table 1. The date of tumor cell inoculation was denoted as day 0.

TABLE 1

Experimental design

| Group | N | Treatment | Dose (mg/kg) | Dosing volume | Dosing Route | Schedule |
|---|---|---|---|---|---|---|
| 1 | 7 | Control Ab | 200 μg/mouse | 100 ul/mouse | i.v. | Dosed on day 3, day 6 of each week |
| 2 | 7 | Vehicle for Compound A | 0 | 5 μl/g | i.v. | Dosed on day 1, day 2 of each week |
| 3 | 7 | Compound A | 14 | 5 μl/g | i.v. | Dosed on day 1, day 2 of each week |
| 4 | 7 | Compound B | 200 μg/mouse | 100 μl/mouse | i.v. | Dosed on day 3, day 6 of each week |
| 5 | 7 | Compound A | 14 | 5 μl/g | i.v. | Dosed on day 1, day 2 of each week |
|   |   | Compound B | 200 μg/mouse | 100 μl/mouse | i.v. | Dosed on day 3, day 6 of each week |

Compound A was formulated in 5% mannitol. Control antibody 6.94 mg/ml rIgG2a and compound B were diluted with PBS to make 0.9 ml dosing solution for each use. For the tumor re-challenge study, mice with complete tumor remission from the previous treatment were re-challenged with CT26 tumor cells ($5\times10^5$ /inoculum) after the tumors were completed regressed for >6 weeks. Treatment nave mice were used as the control. The tumor cells were inoculated subcutaneously at the right upper flank region and tumor growth was followed for another 20 days after the re-challenge.

After inoculation of tumor cells, the animals were checked daily for morbidity and mortality. At the time of routine monitoring, the animals were checked for any effects of tumor growth and treatments on normal behavior such as mobility, visual estimation of food and water consumption, body weight gain/loss (body weights were measured thrice weekly), eye/hair matting and any other abnormal effect. Death and observed clinical signs were recorded.

Tumor volumes were measured 2-3 times weekly in two dimensions using a caliper, and the volume was expressed in $mm^3$ using the formula: $V=0.5\ a\times b^2$ where a and b are the long and short diameters of the tumor, respectively. Tumor weight was measured at study termination. The entire procedures of dosing as well as tumor and body weight measurement were conducted in a Laminar Flow Cabinet.

Sampling procedures: organ and tumor tissues were quickly removed and weighted 3 h post the final dose for FACS, IHC (FFPE), and RNA/pretein expression analysis.

Statistical Analysis: Summary statistics, including mean and the standard error of the mean (SEM), are provided for the tumor volume of each group at each time point. Statistical analysis of difference in tumor volume between the comparing groups was conducted using independent-samples T test. P-values were rounded to three decimal places, with the exception that raw P-values less than 0.001 were stated as P<0.001. All tests were two-sided. P<0.05 was considered to be statistically significant.

Example 1: Synergistic Combinations of Component A and Component B of the Present Invention in the A20 DLBCL Syngeneic Mouse Model with Tumor Intrinsic Regulation of Immunosuppressive Environment and Overcome Resistance to Each Single Agents In clinic, immune-checkpoint blockers showed clinical benefits in melanoma, lung cancer, and Hodgkin's lymphoma (HL), however no activity is observed in non-Hodglin's lymphoma (NHL), such as DLBCL. The anti-tumor activity of Compound A and Compound B was assessed firstly in an immune-checkpoint blocker resistant DLBCL syngeneic A20 xenograft mouse model as single agent and in combination. A20 cells were inoculated subcutaneously at the right flank of female BALB/c mice for tumor development. The treatment was started when the average tumor size reached about 116 $mm^3$. Mice were allocated randomly into experimental groups according to their tumor sizes and being treated from day 12 after tumor cell inoculation. Cpd A was dosed at 14 mg/kg and Cpd B at 200 μg/mouse intravenously with the schedule indicated in FIG. 1 A. Treatment groups were: control antibody (ctrl Ab), vehicle control (vehicle), compound A monotherapy (Cpd. A), Cpd. B monotherapy, 3 combination groups with different dosing schedules. Body weights and tumor size were measured three times per week. Tumor growth curve (FIG. 1B), tumor weight at the end of treatment (FIG. 1C) and tumor response (FIG. 1D) were used as anti-tumor activity endpoints. The tolerability was assessed by body weight change. Furthermore, molecular and celluar mechanisms were investigated by analyzing the effects on tumor cells, immune cells, cytokine/chemokine levels and the expression of signaling moleclules.

Figures 1C, 1D:
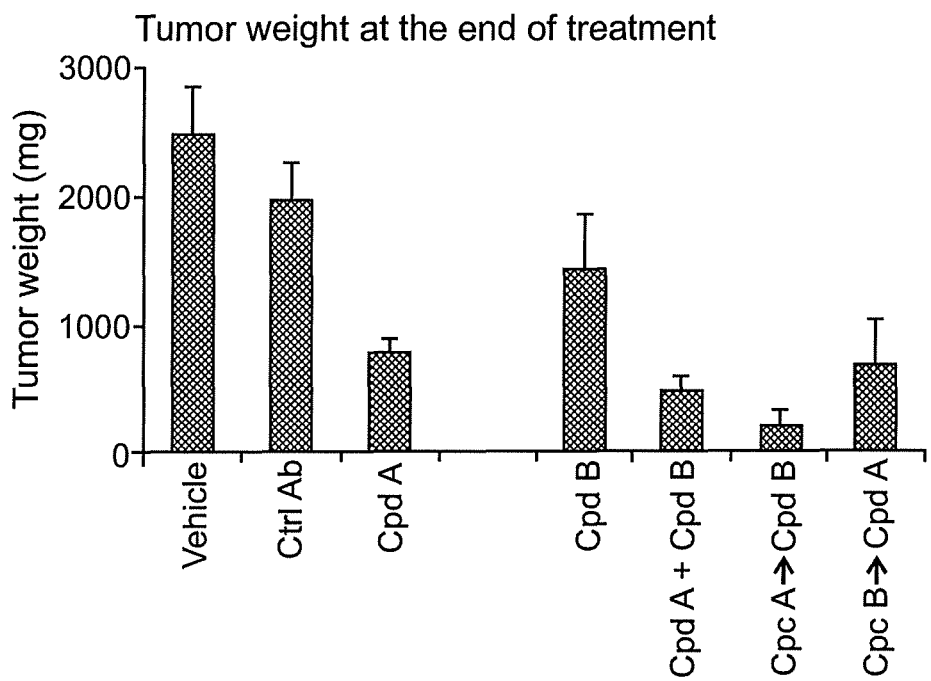
FIG. 1C is a graph that shows tumor weight at the end of treatment with Cpd A and/or Cpd B.
FIG. 1D is a table that shows responses in the A20 tumor model treated with Cpd A and/or Cpd B.
Figure 1E:
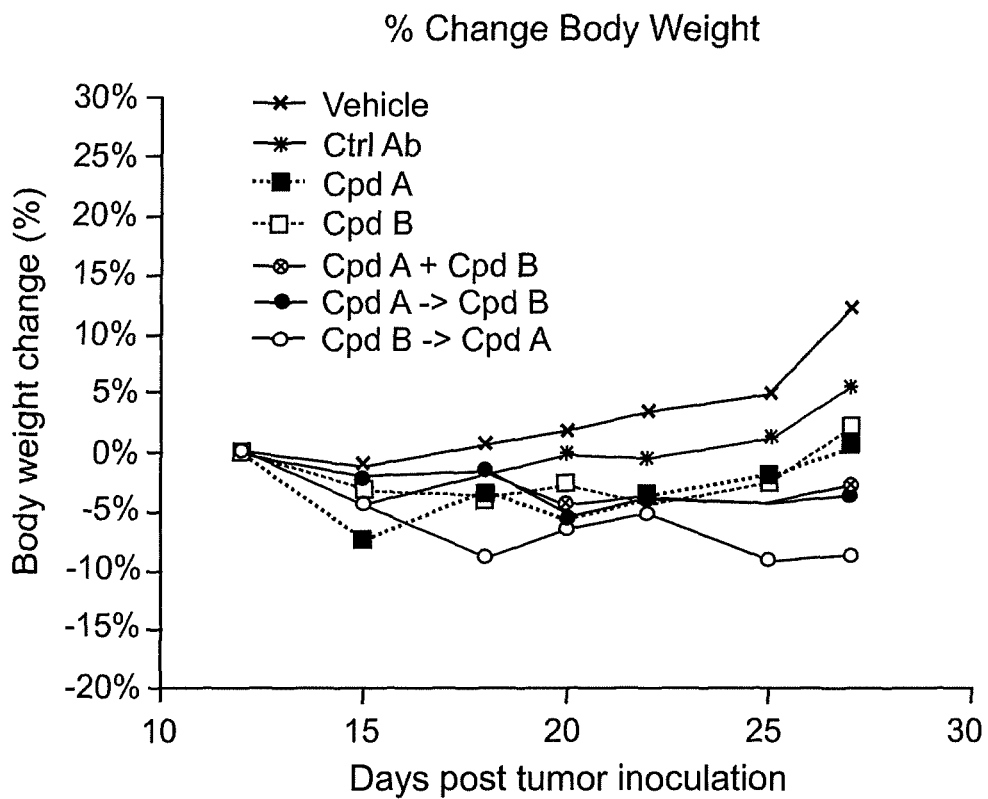
FIG. 1E is a graph that shows percentage of body weight change at days post tumor inoculation in the A20 tumor model treated with Cpd A and/or Cpd B.
Figure 1F:
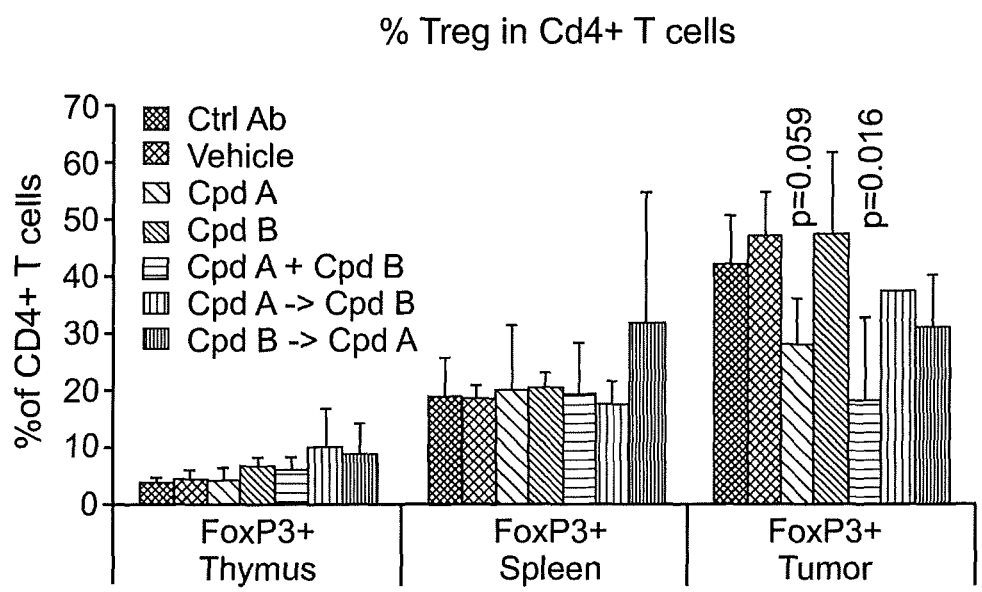
FIG. 1F is a graph that shows percentage of CD4+T cells that are regulatory T cells (Treg) in spleen, thymus, and tumors in the A20 tumor model treated with Cpd A and/or Cpd B.
Figure 1G:
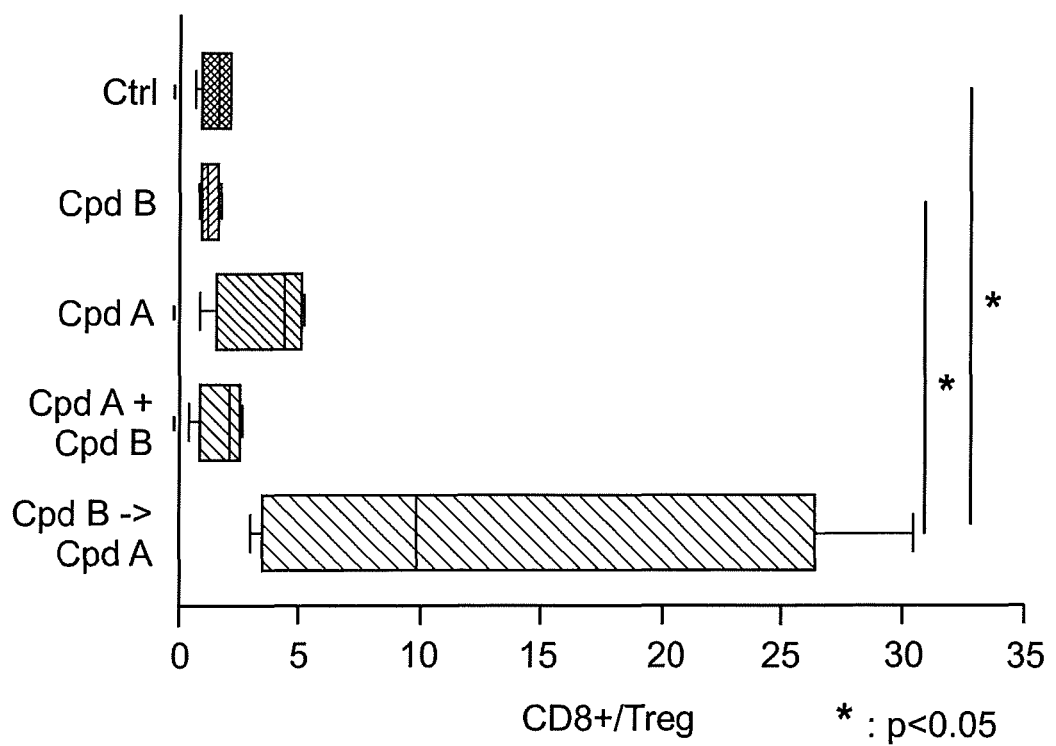
FIG. 1G is a graph that shows the impact of monotherapy and combination therapy with Cpd A and Cpd B on the ratio of cD8+/$T_{reg}$.

FIG. 1A shows 3 different combination schedules during each 1-week treatment cycle. Thus, 1) in group Cpd A+Cpd B, mice were receiving Cpd A on day 1, 2, and Cpd B on day 1, 3, 5; 2) in group Cpd A ➔ Cpd B, mice were treated with Cpd A on day 1, 2 before receiving Cpd B on day 3,5,7; 3) in group Cpd B ➔ Cpd A, Cpd B was given on day 1, 3, 5 and Cpd A was given on day 6,7. In line with clinical observation, immune-checkpoint blocker Cpd B alone did not show significant anti-tumor activity (28% tumor growth inhibition) in vivo in A20 DLBCL syngeneic tumor model. Cpd A as single agent exhibited significant anti-tumor activity with 78% of relative tumor growth inhibition (TGI %) vs vehicle control group. Surprisingly, the efficacy of Cpd A and Cpd B combination is schedule-dependent. Thus, dosing PI3K inhibitor Cpd A prior to the checkpoint blocker Cpd B produced the best efficacy with an average of 96% tumor growth inhibition on day 27 and a partial response rate of 75%, while the combination with the other two schedules did not improve the efficacy (TGI=78% and 71%) compared to Cpd A alone (78% TGI). This result is also in line with the tumor weight measured at the end of the treatment on day 27 (FIG. 1B-D). Overall, combination of Cpd A and Cpd B was tolerated without increasing body weight loss (FIG. 1E). Of note, A20 tumors exhibited high amount of infiltrated T cells, which makes it intriguing that immune checkpoint blocker Cpd B did not show anti-tumor activity. We found here that different from spleen and thymas, immune-suppressive regulatory T cells ($T_{reg}$s) appears to be the major population (42-47%) of the CD4+ T cells in tumors compared to the $T_{reg}$ populations in thymus (~5%) and spleen (~20%). Treatment of Cpd A could specifically reduce the $T_{reg}$ population in tumors, while had minimal or no effects on the $T_{reg}$ in thymus and spleen. This result indicates that Cpd A has unique anti-tumor mechanisms by which targeting tumor and the cross-talk between tumor and the tumor infiltrated immune cells. As the consequence, treatment of Cpd A led to inhibition of immune-suppressive $T_{reg}$ and stimulating anti-tumor immune response, e.g. activation of cytotoxic CD8+ T cells. Interestingly, checkpoint blocker Cpd B did not show effect on $T_{reg}$, explaining lack of efficacy in A20 tumor model in vivo. Importantly, combination of Cpd A and Cpd B could further enhance the inhibitory effects on $T_{reg}$s (FIG. 1F) and increase the ratio of $CD8^+/T_{reg}$ (FIG. 1G), indicating that synergistic anti-tumor activity was achieved at least in one aspect through stimulating T cell-mediated anti-tumor immune responses.

Figure 2A:
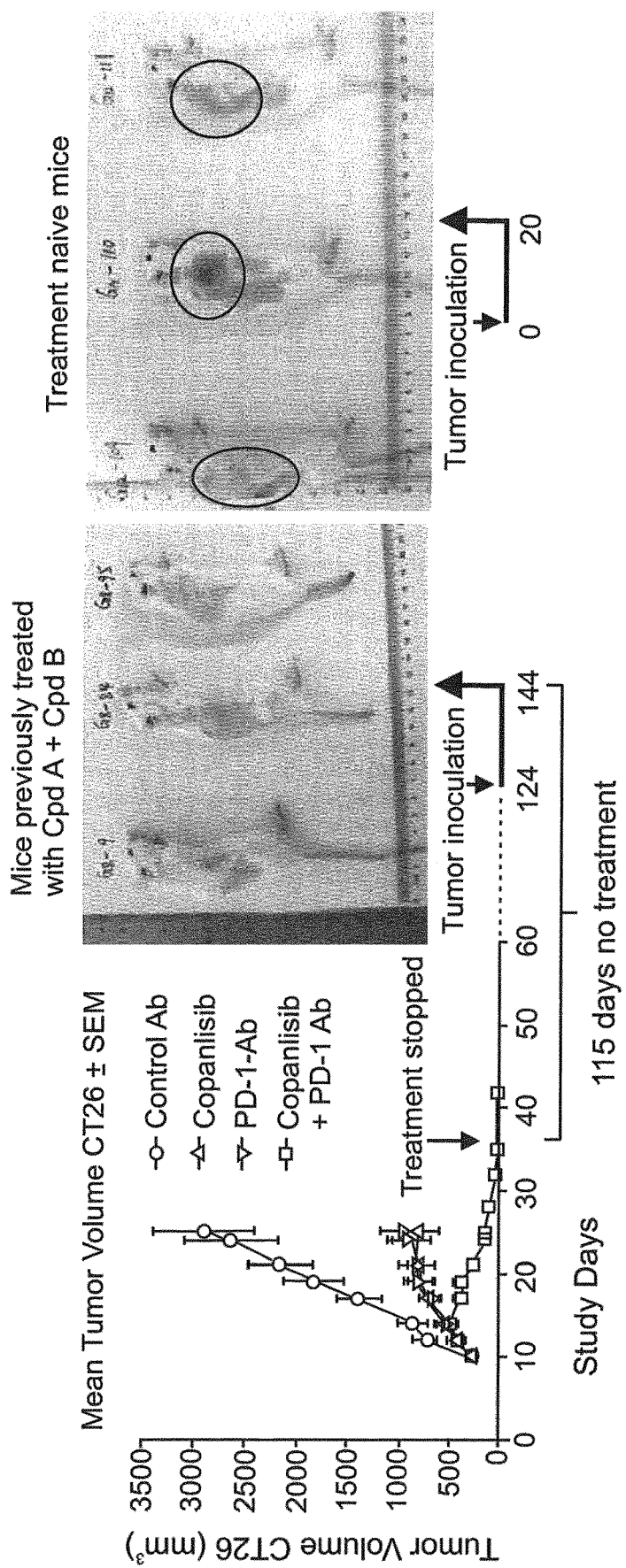
FIG. 2A is a graph of tumor volume versus study days that shows tumor growth in a mouse syngeneic CT26 colorectal cancer xenograft model treated with Cpd A and/or Cpd B.

Example 2: Synergistic Combinations of Component A and Component B of the Present Invention in the Immuno-Checkpoint Blocker Insensitive CT26 Colorectal Cancer Syngeneic Mouse Model Many immune-checkpoint blockers have been tested in colorectal cancer, except a small patient population with $MSI^{high}$ status, the majority of patients did not show responses. Therefore, the anti-tumor activity of Compound A and Compound B was assessed in the mouse syngeneic CT26 ($KRAS^{mut}$, non-$MSI^{high}$) colorectal cancer xenograft model as single agent and in combination. Treatment of Cpd A and Cpd B as monotherapy led to tumor growth delay with 71% and 64% of TGI, respectively (FIGS. 2A and 2B). Synergistic anti-tumor efficacy was observed with 100% tumor responses on Day 36. Thereafter the combination treatment was stopped. Three months later (day 124), CT26 tumor cells were inoculated in the mice previously treated with Cpd A+Cpd B and treatment nave mice were used as the control in a rechallenge study to investigate if tumor-specific memory T cells were generated. After tumor inoculation for 20 days, tumors in treatment nave group reached an average volume of 2168 mm³, while no tumor growth was observed in the animals previously treated with Cpd A+Cpd B combination. This result comfirmed that combination of Cpd A and Cpd B could not only stimulate T cell mediated anti-tumor immune responses but also promote the survival of tumor specific memory T cells. As such, combination of Cpd A and Cpd B is considered as an effective therapeutic approach for the treatment of immune-checkpoint blocker-resistant tumors, such as (but not limited to) colorectal cancer.

In summary, these studies demonstrate that Cpd A has a promising potential in combination with immune-checkpoint blockers to overcome resistance and induce responses in tumors insensitive or resistant to both monotherapies by directly targeting tumors and by stimulating anti-tumor immune responses.

The invention claimed is:

1. A combination of a component A and a component B, wherein:
said component A is 2-amino-N-[7-methoxy-8-(3-morpholin-4-ylpropoxy)-2,3-1,2-c]quinazolin-5-yl]pyrimidine-5-carboxamide
or a physiologically acceptable salt thereof;
and wherein:
said component B is an anti-Programmed Cell Death Protein 1 antibody excluding nivolumab.

2. The combination according to claim 1, wherein:
said component A is 2-amino-N-[7-methoxy-8-(3-morpholin-4-ylpropoxy)-2,3-dihydroimidazo[1,2-c]quinazolin-5-yl]pyrimidine-5-carboxamide.

3. The combination according to claim 1, wherein:
said component A is 2-amino-N-[7-methoxy-8-(3-morpholin-4-ylpropoxy)-2,3-dihydroimidazo[1,2-c]quinazolin-5-yl]pyrimidine-5-carboxamide dihydrochloride.

4. The combination according to claim 1, wherein:
said component B is pembrolizumab, pidilizumab, tislelizumab, MEDI4736, or MPDL3280A.

5. The combination according to claim 2, wherein:
said component B is pembrolizumab, pidilizumab, tislelizumab, MEDI4736, or MPDL3280A.

6. The combination according to claim 3, wherein:
said component B is pembrolizumab, pidilizumab, tislelizumab, MEDI4736, or MPDL3280A.

7. The combination of claim 2, wherein said component B is pembrolizumab.

8. The combination of claim 3, wherein said component B is pembrolizumab.

9. A kit comprising the combination of claim 1.

10. A kit comprising the combination of claim 2.

11. A kit comprising the combination of claim 3.

12. A kit comprising the combination of claim 4.

13. A kit comprising the combination of claim 5.

14. A kit comprising the combination of claim 6.

15. A method for the treatment of cancer, wherein the cancer is selected from the group consisting of lymphoma that is DLBCL and immune-checkpoint blocker insensitive colorectal cancer, comprising administering to a patient in need thereof a therapeutically effective amount of a combination of component A and component B, wherein:
said component A is 2-amino-N-[7-methoxy-8-(3-morpholin-4-ylpropoxy)-2,3-dihydroimidazo[1,2-c]quinazolin-5-yl]pyrimidine-5-carboxamide
or a physiologically acceptable salt thereof;
and wherein:
said component B is an anti-Programmed Cell Death Protein 1 antibody excluding nivolumab.

16. The method of claim 15, wherein:
component A is administered prior to component B.

17. The method of claim 15, wherein:
said component A is 2-amino-N47-methoxy-8-(3-morpholin-4-ylpropoxy)-2,3-dihydroimidazo[1,2-c]quinazolin-5-yl]pyrimidine-5-carboxamide.

18. The method of claim 15, wherein:
said component A is 2-amino-N47-methoxy-8-(3-morpholin-4-ylpropoxy)-2,3-dihydroimidazo[1,2-c]quinazolin-5-yl]pyrimidine-5-carboxamide dihydrochloride.

19. The method of claim 15, wherein:
said component B is pembrolizumab, pidilizumab, tislelizumab, MEDI4736, or MPDL3280A.

20. The method of claim 17, wherein:
said component B is pembrolizumab, pidilizumab, tislelizumab, MEDI4736, or MPDL3280A.
21. The method of claim 18, wherein:
said component B is pembrolizumab, pidilizumab, tislelizumab, MEDI4736, or MPDL3280A.
22. The method of claim 19, wherein:
said component B is pembrolizumab.
23. The method of claim 20, wherein:
said component B is pembrolizumab.
24. The method of claim 21, wherein:
said component B is pembrolizumab.
25. The method of claim 15, wherein the cancer is lymphoma that is DLBCL.
26. The method of claim 19, wherein the cancer is lymphoma that is DLBCL.
27. The method of claim 22, wherein the cancer is lymphoma that is DLBCL.
28. The method of claim 17, wherein the cancer is lymphoma that is DLBCL.
29. The method of claim 23, wherein the cancer is lymphoma that is DLBCL.
30. The method of claim 15, wherein the cancer is immune-checkpoint blocker insensitive colorectal cancer.
31. The method of claim 19, wherein the cancer is immune-checkpoint blocker insensitive colorectal cancer.
32. The method of claim 22, wherein the cancer is immune-checkpoint blocker insensitive colorectal cancer.
33. The method of claim 17, wherein the cancer is immune-checkpoint blocker insensitive colorectal cancer.
34. The method of claim 23, wherein the cancer is immune-checkpoint blocker insensitive colorectal cancer.

* * * * *